US00RE46927E

(19) United States
(12) Reissued Patent
Leinsing et al.

(10) Patent Number: US RE46,927 E
(45) Date of Reissued Patent: Jul. 3, 2018

(54) HEART BAND WITH FILLABLE CHAMBERS TO MODIFY HEART VALVE FUNCTION

(71) Applicant: Mardil, Inc., Plymouth, MN (US)

(72) Inventors: Karl R. Leinsing, Dover, NH (US); Jaishankar Raman, Chicago, IL (US)

(73) Assignee: Mardil, Inc., Plymouth, MN (US)

(21) Appl. No.: 14/152,810

(22) Filed: Jan. 10, 2014

Related U.S. Patent Documents

Reissue of:
(64) Patent No.: 8,092,363
Issued: Jan. 10, 2012
Appl. No.: 11/899,253
Filed: Sep. 5, 2007

(51) Int. Cl.
*A61N 1/362* (2006.01)
*A61F 2/24* (2006.01)

(52) U.S. Cl.
CPC ..... *A61F 2/2481* (2013.01)

(58) Field of Classification Search
CPC ..... A61F 2/2481
USPC ..... 600/16, 17; 623/3.16, 3.2
See application file for complete search history.

(56) References Cited

U.S. PATENT DOCUMENTS

| | | | |
|---|---|---|---|
| 3,587,567 | A | 6/1971 | Schiff |
| 3,983,863 | A | 10/1976 | Janke et al. |
| 4,048,990 | A | 9/1977 | Goetz |
| 4,403,604 | A | 9/1983 | Wilkinson et al. |
| 4,428,375 | A | 1/1984 | Ellman |
| 4,536,893 | A | 8/1985 | Parravicini |
| 4,630,597 | A | 12/1986 | Kantrowitz et al. |
| 4,690,134 | A | 9/1987 | Snyders |
| 4,821,723 | A | 4/1989 | Baker, Jr. et al. |
| 4,878,890 | A | 11/1989 | Bilweis |
| 4,936,857 | A | 6/1990 | Kulik |
| 4,957,477 | A | 9/1990 | Lundback |
| 4,973,300 | A | 11/1990 | Wright |
| 4,976,730 | A | 12/1990 | Kwan-Gett |
| 5,057,117 | A | 10/1991 | Atweh |
| 5,087,243 | A | 2/1992 | Avitall |

(Continued)

FOREIGN PATENT DOCUMENTS

| | | |
|---|---|---|
| WO | WO98/14136 | 4/1998 |
| WO | WO9814136 A1 | 4/1998 |

(Continued)

OTHER PUBLICATIONS

Bolling,et al., "Intermediate-Term Outcome of Mitral Reconstruction in Cardiomyopathy", *J. Thorac. Cardiovasc. Sur.*, vol. 115:2 (381-8) Feb. 1998.

(Continued)

*Primary Examiner* — Jeffrey R Jastrzab
(74) *Attorney, Agent, or Firm* — Fish & Richardson P.C.

(57) ABSTRACT

The present invention relates to an external heart device, having a layered band dimensioned to be received around a patient's heart, which also includes at least one fillable chamber between the layers in the band that functions to apply localized pressure to the outside of the heart when filled. More particularly, the fillable chambers are positioned such that they exert an inward radial force on a heart valve. Areas between the fillable chambers may also be sized and positioned to form a bridge of little to no pressure over the vascular structures of the heart.

48 Claims, 16 Drawing Sheets

(56) References Cited

U.S. PATENT DOCUMENTS 5,131,905 A 7/1992 Grooters
5,150,706 A 9/1992 Cox et al.
5,186,711 A 2/1993 Epstein
5,192,314 A 3/1993 Daskalakis
5,256,132 A 10/1993 Snyders
5,290,217 A 3/1994 Campos
5,356,432 A 10/1994 Rutkow et al.
5,383,840 A 1/1995 Heilman et al.
5,385,156 A 1/1995 Oliva
5,429,584 A 7/1995 Chiu
5,507,779 A 4/1996 Altman
5,524,633 A 6/1996 Heaven et al.
5,558,617 A 9/1996 Heilman et al.
5,603,337 A 2/1997 Jarvik
5,647,380 A 7/1997 Campbell et al.
5,702,343 A 12/1997 Alferness
5,713,954 A 2/1998 Rosenberg et al.
5,800,528 A 9/1998 Lederman et al.
5,961,440 A 10/1999 Schweich, Jr. et al.
5,976,551 A 11/1999 Mottez et al.
6,045,497 A 4/2000 Schweich, Jr. et al.
6,050,936 A 4/2000 Schweich, Jr. et al.
6,059,715 A 5/2000 Schweich, Jr. et al.
6,076,013 A 6/2000 Brennan et al.
6,077,214 A 6/2000 Mortier et al.
6,077,218 A 6/2000 Alferness
6,085,754 A 7/2000 Alferness et al.
6,123,662 A 9/2000 Alferness
6,126,590 A 10/2000 Alferness
6,155,968 A 12/2000 Wilk
6,155,972 A 12/2000 Nauertz et al.
6,162,168 A 12/2000 Schweich, Jr. et al.
6,165,119 A 12/2000 Schweich, Jr. et al.
6,165,120 A 12/2000 Schweich, Jr. et al.
6,165,121 A 12/2000 Alferness
6,165,122 A 12/2000 Alferness
6,169,922 B1 1/2001 Alferness et al.
6,174,279 B1 1/2001 Girard
6,179,791 B1 1/2001 Krueger
6,183,411 B1 2/2001 Mortier et al.
6,190,408 B1 2/2001 Melvin
6,193,646 B1 2/2001 Kulisz et al.
6,206,820 B1 3/2001 Kazi
6,221,103 B1 4/2001 Melvin
6,230,714 B1 5/2001 Alferness et al.
6,241,654 B1 6/2001 Alferness
6,260,552 B1 7/2001 Mortier et al.
6,261,222 B1 7/2001 Schweich, Jr. et al.
6,264,602 B1 7/2001 Mortier et al.
6,293,906 B1 9/2001 Vanden Hoek et al.
6,332,863 B1 12/2001 Schweich, Jr. et al.
6,332,864 B1 12/2001 Schweich, Jr. et al.
6,332,893 B1 12/2001 Mortier et al.
6,370,429 B1 4/2002 Alferness et al.
6,375,608 B1 4/2002 Alferness
6,402,679 B1 6/2002 Mortier
6,402,680 B2 6/2002 Mortier
6,406,420 B1 6/2002 McCarthy et al.
6,409,760 B1 6/2002 Melvin
6,416,459 B1 7/2002 Haindl
6,425,856 B1 7/2002 Shapland et al.
6,432,039 B1 8/2002 Wardle
6,482,146 B1 11/2002 Alferness et al.
6,488,618 B1 12/2002 Paolitto et al.
6,494,825 B1 12/2002 Talpade
6,508,756 B1 1/2003 Kung et al.
6,514,194 B2 2/2003 Schweich, Jr. et al.
6,520,904 B1 2/2003 Melvin
6,537,198 B1 3/2003 Vidlund et al.
6,537,203 B1 3/2003 Alferness et al.
6,544,168 B2 4/2003 Alferness
6,547,716 B1 4/2003 Milbocker
6,558,319 B1 5/2003 Aboul-Hosn et al.
6,564,094 B2 5/2003 Alferness et al.
6,567,699 B2 5/2003 Alferness et al.
6,569,082 B1 5/2003 Chin
6,572,533 B1 6/2003 Shapland et al.
6,572,534 B1 * 6/2003 Milbocker ..... A61F 2/2481 600/16
6,575,921 B2 6/2003 Vanden Hoek et al.
6,579,226 B2 6/2003 Vanden Hoek et al.
6,582,355 B2 6/2003 Alferness et al.
6,587,734 B2 7/2003 Okuzumi et al.
6,589,160 B2 7/2003 Schweich, Jr. et al.
6,592,514 B2 7/2003 Kolata et al.
6,595,912 B2 7/2003 Lau et al.
6,602,184 B2 8/2003 Lau et al.
6,612,978 B2 9/2003 Lau et al.
6,612,979 B2 9/2003 Lau et al.
6,616,596 B1 9/2003 Milbocker
6,616,684 B1 9/2003 Vidlund et al.
6,622,730 B2 9/2003 Ekvall et al.
6,626,821 B1 * 9/2003 Kung ..... A61M 1/1068 600/16
6,629,921 B1 10/2003 Schweich, Jr. et al.
6,645,139 B2 11/2003 Haindl
6,663,558 B2 12/2003 Lau et al.
6,673,009 B1 1/2004 Vanden Hoek et al.
6,682,474 B2 1/2004 Lau et al.
6,682,475 B2 1/2004 Cox et al.
6,682,476 B2 1/2004 Alferness et al.
6,685,627 B2 2/2004 Jayaraman
6,689,048 B2 2/2004 Vanden Hoek et al.
6,695,768 B1 2/2004 Levine et al.
6,695,769 B2 2/2004 French et al.
6,701,929 B2 3/2004 Hussein
6,702,732 B1 3/2004 Lau et al.
6,709,382 B1 3/2004 Horner
6,716,158 B2 4/2004 Raman et al.
6,723,038 B1 4/2004 Schroeder et al.
6,723,041 B2 4/2004 Lau et al.
6,726,696 B1 4/2004 Houser et al.
6,726,920 B1 4/2004 Theeuwes et al.
6,730,016 B1 5/2004 Cox et al.
6,746,471 B2 6/2004 Mortier et al.
6,755,777 B2 6/2004 Schweich, Jr. et al.
6,755,779 B2 6/2004 Vanden Hoek et al.
6,755,861 B2 6/2004 Nakao
6,764,510 B2 7/2004 Vidlund et al.
6,776,754 B1 8/2004 Wilk
6,793,618 B2 9/2004 Schweich, Jr. et al.
6,808,488 B2 10/2004 Mortier et al.
6,852,075 B1 2/2005 Taylor
6,852,076 B2 2/2005 Nikolic et al.
6,858,001 B1 2/2005 Aboul-Hosn
6,876,887 B2 4/2005 Okuzumi et al.
6,881,185 B2 4/2005 Vanden Hock et al.
6,896,652 B2 5/2005 Alferness et al.
6,902,522 B1 6/2005 Walsh et al.
6,902,524 B2 * 6/2005 Alferness et al. ..... 600/37
6,997,865 B2 2/2006 Alferness et al.
7,022,064 B2 4/2006 Alferness et al.
7,025,719 B2 4/2006 Alferness et al.
7,077,862 B2 7/2006 Vidlund et al.
7,112,219 B2 9/2006 Vidlund
7,276,022 B2 10/2007 Lau et al.
7,468,029 B1 12/2008 Robertson
2001/0016675 A1 8/2001 Mortier et al.
2001/0025171 A1 9/2001 Mortier et al.
2002/0029080 A1 3/2002 Mortier et al.
2002/0058855 A1 5/2002 Schweich, Jr. et al.
2002/0068849 A1 6/2002 Schweich, Jr. et al.
2002/0068850 A1 6/2002 Vanden Hoek et al.
2002/0077524 A1 6/2002 Schweich, Jr. et al.
2002/0147406 A1 10/2002 Von Segesser
2002/0169358 A1 11/2002 Mortier et al.
2002/0169359 A1 11/2002 McCarthy et al.
2002/0169360 A1 11/2002 Taylor et al.
2002/0173694 A1 11/2002 Mortier et al.
2003/0032979 A1 2/2003 Mortier et al.
2003/0050529 A1 3/2003 Vidlund et al.
2003/0065248 A1 4/2003 Lau et al.
2003/0088149 A1 5/2003 Raman et al.
2003/0130731 A1 7/2003 Vidlund et al.

(56) References Cited

U.S. PATENT DOCUMENTS

| | | | | |
|---|---|---|---|---|
| 2003/0166992 | A1 | 9/2003 | Schweich, Jr. et al. | |
| 2003/0171641 | A1 | 9/2003 | Schweich, Jr. et al. | |
| 2003/0181928 | A1 | 9/2003 | Vidlund et al. | |
| 2003/0229265 | A1* | 12/2003 | Girard | A61F 2/2481 600/37 |
| 2003/0233023 | A1 | 12/2003 | Khaghani et al. | |
| 2004/0002626 | A1 | 1/2004 | Feld et al. | |
| 2004/0010180 | A1 | 1/2004 | Scorvo | |
| 2004/0034272 | A1 | 2/2004 | Diaz et al. | |
| 2004/0064014 | A1* | 4/2004 | Melvin | A61F 2/2487 600/37 |
| 2004/0127983 | A1 | 7/2004 | Mortier et al. | |
| 2004/0133062 | A1 | 7/2004 | Pai et al. | |
| 2004/0133063 | A1 | 7/2004 | McCarthy et al. | |
| 2004/0147805 | A1 | 7/2004 | Lau et al. | |
| 2004/0147965 | A1 | 7/2004 | Berger | |
| 2004/0167374 | A1 | 8/2004 | Schweich et al. | |
| 2004/0181118 | A1 | 9/2004 | Kochamba | |
| 2004/0181120 | A1 | 9/2004 | Kochamba | |
| 2004/0181124 | A1 | 9/2004 | Alferness | |
| 2004/0186342 | A1 | 9/2004 | Vanden Hock et al. | |
| 2004/0210104 | A1 | 10/2004 | Lau et al. | |
| 2004/0215308 | A1 | 10/2004 | Bardy et al. | |
| 2004/0225304 | A1 | 11/2004 | Vidlund et al. | |
| 2004/0243229 | A1 | 12/2004 | Vidlund et al. | |
| 2004/0249242 | A1 | 12/2004 | Lau et al. | |
| 2004/0267083 | A1 | 12/2004 | McCarthy et al. | |
| 2004/0267329 | A1 | 12/2004 | Raman et al. | |
| 2005/0004428 | A1 | 1/2005 | Cox et al. | |
| 2005/0010079 | A1 | 1/2005 | Bertolero et al. | |
| 2005/0014992 | A1 | 1/2005 | Lilip et al. | |
| 2005/0020874 | A1 | 1/2005 | Lau et al. | |
| 2005/0033109 | A1 | 2/2005 | Lau et al. | |
| 2005/0038316 | A1 | 2/2005 | Taylor | |
| 2005/0054892 | A1 | 3/2005 | Lau et al. | |
| 2005/0058853 | A1 | 3/2005 | Kochambe | |
| 2005/0059854 | A1 | 3/2005 | Hoek et al. | |
| 2005/0065396 | A1 | 3/2005 | Mortier et al. | |
| 2005/0075723 | A1 | 4/2005 | Schroeder et al. | |
| 2005/0085688 | A1 | 4/2005 | Girard et al. | |
| 2005/0090707 | A1 | 4/2005 | Lau et al. | |
| 2005/0133941 | A1* | 6/2005 | Schuhmacher | 257/E51.027 |
| 2005/0171589 | A1 | 8/2005 | Lau et al. | |
| 2005/0192474 | A1 | 9/2005 | Vanden Hoek et al. | |
| 2005/0283042 | A1* | 12/2005 | Meyer et al. | 600/37 |
| 2006/0063970 | A1 | 3/2006 | Raman et al. | A61F 2/2481 600/37 |
| 2007/0043416 | A1 | 2/2007 | Callas et al. | |
| 2008/0064917 | A1* | 3/2008 | Bar et al. | 600/16 |

FOREIGN PATENT DOCUMENTS

| | | | |
|---|---|---|---|
| WO | WO 1999/44534 | | 9/1999 |
| WO | WO9852470 | A1 | 10/1999 |
| WO | WO9952471 | A1 | 10/1999 |
| WO | WO 2000/06027 | | 2/2000 |
| WO | WO 2000/06028 | | 2/2000 |
| WO | WO0028912 | A1 | 5/2000 |
| WO | WO0028918 | A1 | 5/2000 |
| WO | WO0103608 | A1 | 1/2001 |
| WO | WO0110421 | A1 | 2/2001 |
| WO | WO0191667 | A3 | 12/2001 |
| WO | WO0195830 | A2 | 12/2001 |
| WO | WO0213726 | A2 | 2/2002 |
| WO | WO02000099 | A3 | 9/2002 |
| WO | WO03022131 | A2 | 3/2003 |
| WO | WO 2004/043265 | | 5/2004 |

OTHER PUBLICATIONS

Bourge, "Clinical Trial Begins for Innovative Device-Altering Left Ventricular Shape in Heart Failure", *UAB Insight*, http://www.health.uab.edu/show, posted Aug. 8, 2002.

Ghanta, et al., "Cardiovascular Surgery: Adjustable, Physiological Ventricular Restraint Improves Left Ventricular Mechanics and Reduces Dilation in an Ovine Model of Chronic Heart Failure," *Circulation, JAHA*, 2007, vol. 115 (1201-10).

Hung, et al., "Persistent Reduction of Ischemic Mitral Regurgitation by Papillary Muscle Repositioning: Structural Stabilization of the Pipillary Muscle Ventricular Wall Complex," *Circulation, JAHA*, 2007, vol. 116 (I-259 I-263).

Lamas, et al., "Clinical Significance of Mitral Regurgitation After Acute Myocardial Infarction", *Circulation—JAHA*, vol. 96:3 (827-33) Aug. 5, 1997.

Liel-Cohen, et al., "Design of a New Surgical Approach for Ventricular Remodeling to Relieve Ischemic Mitral Regurgitation," *Circulation 2000*, vol. 101(2756-63).

Pai, et al., "Valvular Egurgitation," *Clinical Science 2000*, Abstracts 1800-1804.

Timek, et al., "Pathogenesis of Mitral Regurgitation in Tachycaria Induced Cardiomyopathy," *Circulation—JAHA*, 2001, 104 (I-47 I-53).

Lei-Cohen, et al., "Design of a New Surgical Approach for Ventricular Remodeling to Relieve Ischemic Mitral Regurgitation," Circulation Jun. 13, 2000, vol. 101, pp. 2756-2763.

* cited by examiner

HEART BAND WITH FILLABLE CHAMBERS TO MODIFY HEART VALVE FUNCTION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to devices and methods for treating dilatation of heart valves by applying localized pressure to surface areas of the heart.

BACKGROUND OF THE INVENTION

Dilatation of the base of the heart occurs with various diseases of the heart and often is a causative mechanism of heart failure. In some instances, depending on the cause, the dilatation may be localized to one portion of the base of the heart (e.g., mitral insufficiency as a consequence of a heart attack affecting the inferior and basal wall of the left ventricle of the heart), thereby affecting the valve in that region. In other cases, such as cardiomyopathy, the condition may be global affecting more of the heart and its base, causing leakage of particularly the mitral and tricuspid valves. Other conditions exist where the mitral valve structure is abnormal, predisposing to leakage and progressive dilatation of the valve annulus (area of valve attachment to the heart). This reduces the amount of blood being pumped out by the ventricles of the heart, thereby impairing cardiac function further.

In patients with heart failure and severe mitral insufficiency, good results have been achieved by aggressively repairing mitral and/or tricuspid valves directly, which requires open-heart surgery (Bolling, et al). The mitral valve annulus is reinforced internally by a variety of prosthetic rings (Duran Ring, Medtronic Inc) or bands (Cosgrove-Edwards Annuloplasty Band, Edwards Lifesciences Inc). The present paradigm of mitral valve reconstruction is therefore repair from inside the heart, with the annulus being buttressed or reinforced by the implantation of a prosthetic band or ring. Since this is major open-heart surgery with intra-cavitary reconstruction, there is the attendant risk of complications and death associated with mitral valve surgery. Another approach has been to replace the mitral valve, which while addressing the problem, also requires open-heart surgery and involves implantation of a bulky artificial, prosthetic valve with all its consequences. Because every decision to perform major surgery requires some risk vs. benefit consideration, patients get referred for risky surgery only when they are significantly symptomatic or their mitral valve is leaking severely.

In contrast to the more invasive approaches discussed above, in specific instances of inferior left ventricular wall scarring causing mitral regurgitation, Liel-Cohen and co-workers have suggested localized pressure or support of the bulging scar of the inferior wall of the heart from the outside (Liel-Cohen. N. et al. (2000) "Design of a new surgical approach for ventricular remodeling to relieve ischemic mitral regurgitation: insights from 3-dimensional echocardiography". Circulation 101 (23):2756-2763).

Another less invasive approach to preventing global heart dilation is ventricular containment with a custom made polyester mesh, or cardiac support device (U.S. Pat. Nos. 6,077,218 and 6,123,662). These devices are designed to provide a passive constraint around both ventricles of the heart, and constrain diastolic expansion of the heart. Other devices include ventricular assist devices that provide cardiac assistance during systole and dynamic ventricular reduction devices that actively reduce the size of the heart. However, this technique does not specifically address valve leakage using a device that reinforces the base of the heart in all phases of the cardiac cycle.

Percutaneous approaches (including "edge-to-edge", placating the annulus and coronary sinus approaches) of accessing the heart through the femoral artery have been used. Disadvantages of percutaneous approaches include fixture-made-clots being sent downstream, and the dangers of potential patient allergy to contrast media. In addition, percutaneous approaches require complicated systems and are very dependent on the anatomy of the patient. As a result these systems require the help of an experienced and trained interventional cardiologist to assist with the procedure.

An example of a system that provides a less invasive approach to base stabilization is found in U.S. Pat. No. 6,716,158 to Raman et. al. However, although the Raman et. al. system operates to stabilize the base of the heart, it does not provide a system to modulate or modify heart valve function by applying localized pressure to particular regions of the heart, for example, to tissues adjacent to heart valve. Such a system would advantageously apply inward pressure to tissue adjacent to the heart valves so as to modify the shape or reduce the size of a heart valve itself. Accordingly, there is a need to non-invasively repair or re-configure the shape of a mitral and/or tricuspid valve so as to treat valve dilation and resulting valve insufficiency problems.

The present invention is directed to solving the above mentioned problems and can advantageously be applied to both patient populations requiring heart valve modification by applying localized pressure, and to patient populations simply requiring external stabilization of the base of the heart.

SUMMARY OF THE INVENTION

The present invention addresses the problems discussed above by providing a device for the treatment of certain heart disorders, in particular mitral and/or tricuspid valve insufficiency. The device aims to apply localized pressures to the heart and/or reduce the size of the base of the heart that contains these valvular structures. The device also provides a system for applying inward pressure to tissue adjacent to the heart valves so as to shape the mitral and/or tricuspid valve itself. In addition, the present invention can be used to address progressive dilatation of any localized area of the heart, such as the atrial or ventricular myocardium, or the cardiac base. It does so by optionally providing external re-enforcement or remodeling of the cardiac base while still providing support of the valve at annular and sub-annular levels. As used herein, the surgical procedure for implanting the device is referred to as basal annuloplasty of the cardia externally (BACE™) and the device is referred to as the external cardiac basal annuloplasty system BACE System.

An advantage of the present system is that it overcomes the disadvantages of percutaneous approaches by overcoming the disadvantages of systems accessing the heart through the femoral artery.

Another advantage of the present invention is that it remodels the heart while re-shaping the valve(s). As such, the present invention operates to both prevent heart disease and to treat it as well. In addition, in one embodiment of the present invention uniquely incorporates the use of subcutaneous ports that allows adjustment and post operative re-shaping of the valve(s) without making incisions in the patient.

In one aspect, the present invention provides an external heart device, comprising: a band dimensioned to be received around a patient's heart, the band comprising an inner layer and an outer layer, wherein areas of the inner layer and outer layer are bound to one another; and at least one fillable chamber in the band, the at least one fillable chamber being located in areas where the inner layer and the outer layer are not bound to one another.

In various embodiments, the at least one fillable chamber may either be formed or inserted into the areas where the inner layer and the outer layer are not bound to one another, thereby providing a band structure with one or more integral fillable chambers.

In various embodiments, the band may be transparent, and may optionally be made of silicone rubber, or other suitable bio compatible implantable material.

In various embodiments, the present invention may be formed with the inner layer and outer layer being bound to one another by adhesives, crosslinking, heat and/or pressure, or even by stitching.

In various embodiments, the interior surface of the inner layer may optionally be textured so as to remain in position around the heart, yet still permit the device to be removed in future without damaging the surface of the heart.

In various embodiments, the device has a plurality of fillable chambers, with two of the fillable chambers being positioned spaced apart from one another, and with the band forming a bridge portion therebetween. Advantageously, the bridge portion in the band may be dimensioned to be positioned over vasculature on the exterior of the heart when at least one of the fillable chambers are filled.

Advantageously as well, the dimensions of the fillable chambers and their positioning in the band may also provide a system to apply inward pressure to tissues adjacent to a heart valve so as to modify or change the shape of the valve to a more desired shape. In one exemplary application of the present invention, two of the fillable chambers are positioned on opposite sides of a mitral valve of the heart to shape the mitral valve to prevent mitral valve dilation, and resulting mitral regurgitation.

In various embodiments, each of the fillable chambers has a filling tube in fluid communication therewith. In different embodiments, the filling tubes may optionally be fillable through a blunt needle port, a sharp needle port, or through a subcutaneous port, Luer port fitting, or various combinations thereof. In one exemplary embodiment, all but one of the filling tubes are fillable through a subcutaneous port, and the plurality of subcutaneous ports are disposed together on a sheet. The sheet may optionally be made of silicone or polyester or other suitable material and may be used to position these subcutaneous ports at a convenient location within the patient's body.

The filling tubes may optionally be made of silicone or other suitable bio-implantable material. Depending upon the method of manufacturing the present device, the individual filling tubes may be integrally formed as the filling chambers of the device are formed, or they may be inserted after the fillable chambers have been formed.

In various embodiments and applications, the various fillable chambers may be filled either by saline, a hardening polymer, a gel, a gas, or other suitable material.

In optional embodiments, one or more sleeves may be positioned around an exterior surface of the outer layer of the device. Such sleeves may advantageously operate to hold the band at a preferred location on the patient's heart. Specifically, such sleeves are designed to promote tissue ingrowth to hold the device in place. These sleeves may be made of polyester or other suitable materials. In one exemplary embodiment, they are ⅝" wide, however, the present invention is not limited to any particular dimensions.

In one exemplary embodiment, the band may be between 2 and 5 cms wide and may be secured by clips, sutures, or other fasteners, with some on the posterior side and some on the anterior side of the heart. Specific care is taken to avoid injury to the circumflex and right coronary arteries and the coronary sinus. This procedure may be performed either as a stand-alone procedure or as an adjunct to other cardiac surgery. Additionally, it may be performed with or without the aid of cardio-pulmonary bypass.

Optional variations of the device include a complete stabilization of the base of the heart, or a partial stabilization around the expansile portions of the mitral and tricuspid valves. It is to be understood, however, that the present invention is not simply directed to stabilizing the base of the heart. Instead, the present invention is well suited to modifying heart valve function (and optional valve re-shaping) by therapeutically applying localized pressures to various regions of the heart.

Another variation seeks to use ports along the device that will facilitate delivery of specialized drugs, gene therapeutic agents, growth factors, etc.

A specific variation incorporates the use of epicardial biventricular, and multi-site pacing electrodes implanted along with the BACE-System, where multi-site pacing might be indicated. One iteration has multiple electrodes arranged as an array along the left and right ventricular walls of the heart, close to the base of the heart. The option then exists to allow selection of various sites along the heart to allow for optimal resynchronisation or optimization of contractility.

The present invention also provides a method of implantation, which may be through a conventional full median stemotomy with the strip being secured by sutures, or a minimally invasive thoracotomy approach whereby the device/strip may be folded/rolled and implanted by a specialized implantation system and secured using adhesives, self-firing clips, sutures, etc.

Another application of the device is the local application to stabilize scars of the heart to prevent their expansion (local ventricular stabilization).

As depicted in FIGS. 7A to 7D, PV=pulmonary valve, MV=mitral valve, AV=aortic valve and TV=tricuspid valve.

Figure 7A:
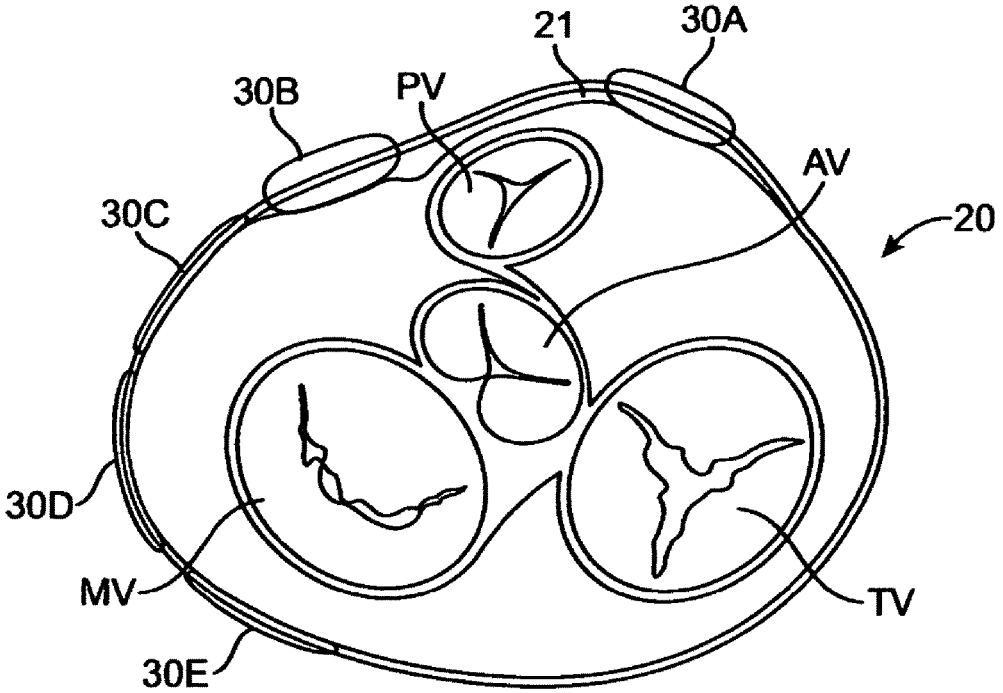

FIG. 7A depicts a cross-sectional schematic diagram of the base of the heart showing the present invention prior to re-shaping the mitral valve by filling chamber 30E.

Figure 7B:
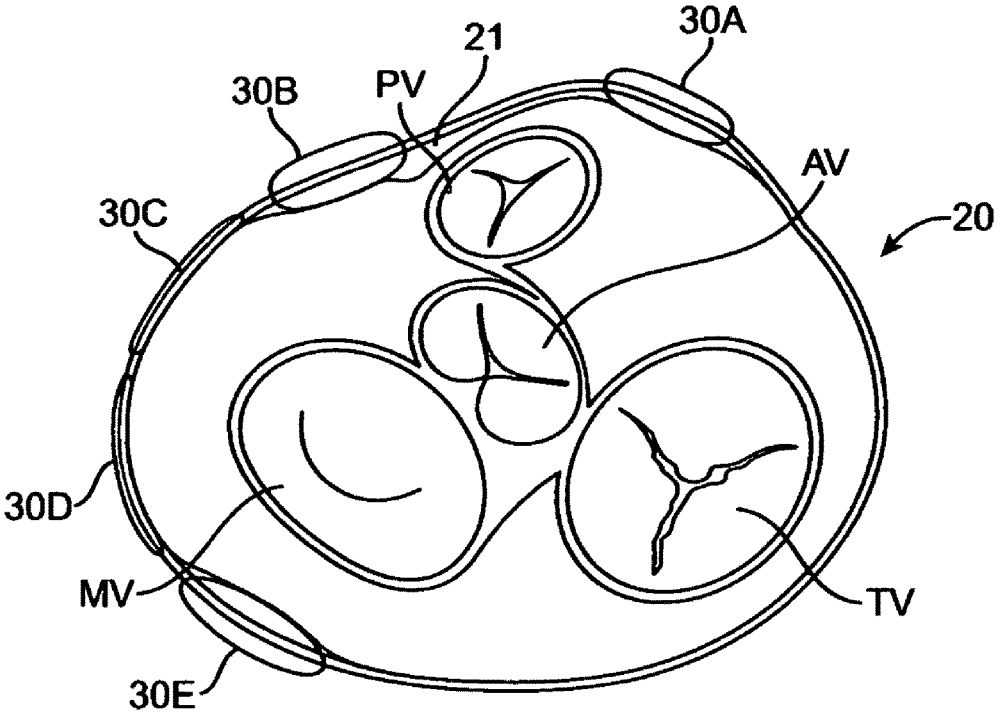

FIG. 7B depicts a cross-sectional schematic diagram of the base of the heart showing the present invention after re-shaping the mitral valve by filling chamber 30E (i.e.: showing the band forming a bridge portion between two of the fillable chambers 30A and 30B, and showing the modification of the shape of a patient's mitral valve to treat mitral dilation.)

Figure 7C:
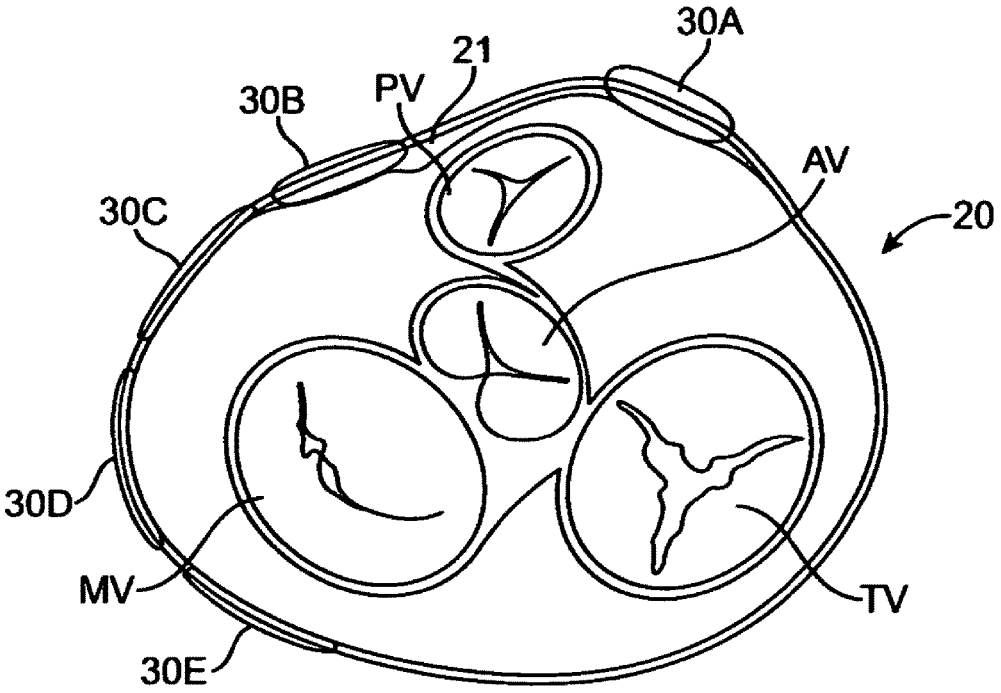

FIG. 7C depicts a cross-sectional schematic diagram of the base of the heart showing the present invention prior to re-shaping the mitral valve by filling chamber 30D.

Figure 7D:
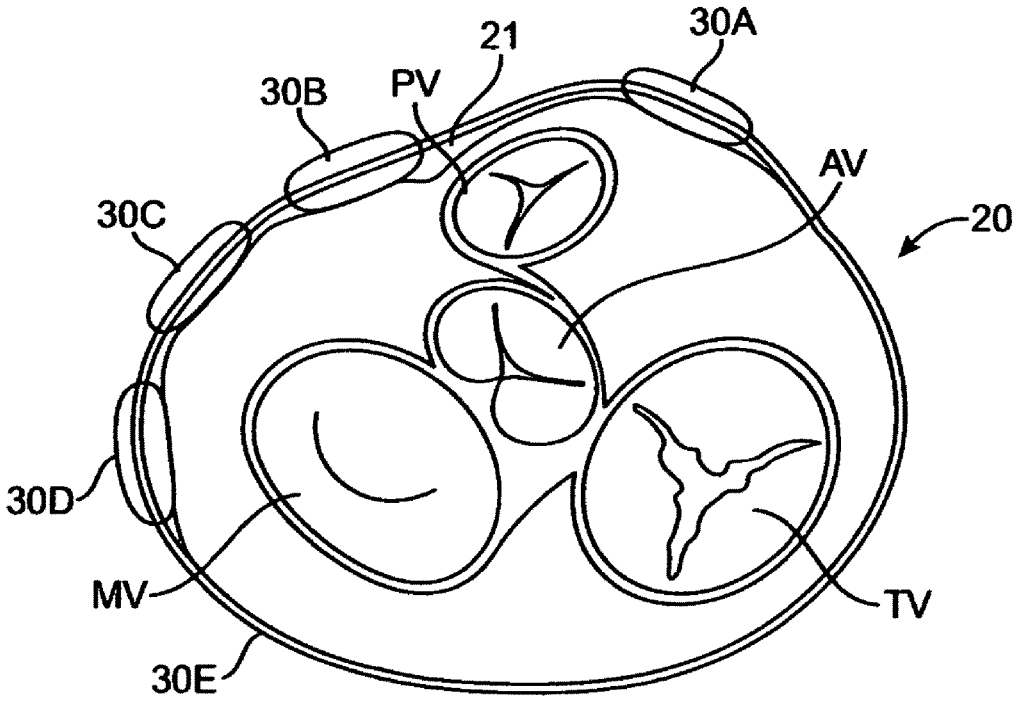

FIG. 7D depicts a cross-sectional schematic diagram of the base of the heart showing the present invention after re-shaping the mitral valve by filling chamber 30D (i.e., showing the band forming a bridge portion between two of the fillable chambers 30A and 30B, and showing the modification of the shape of a patient's mitral valve to treat mitral dilation.)

Figure 8:
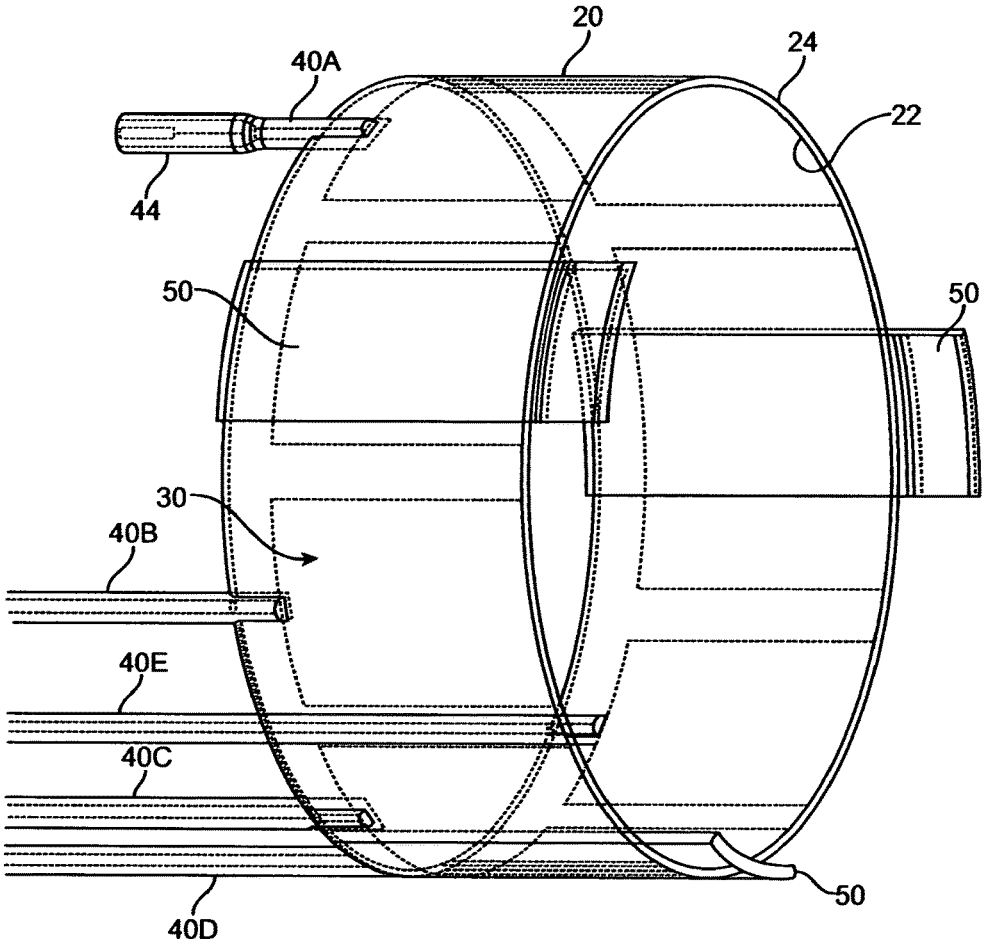

FIG. 8 is a perspective view of a second representative embodiment of the device of the present invention three sleeves received around the band for attachment to the exterior of the heart.

Figure 9:
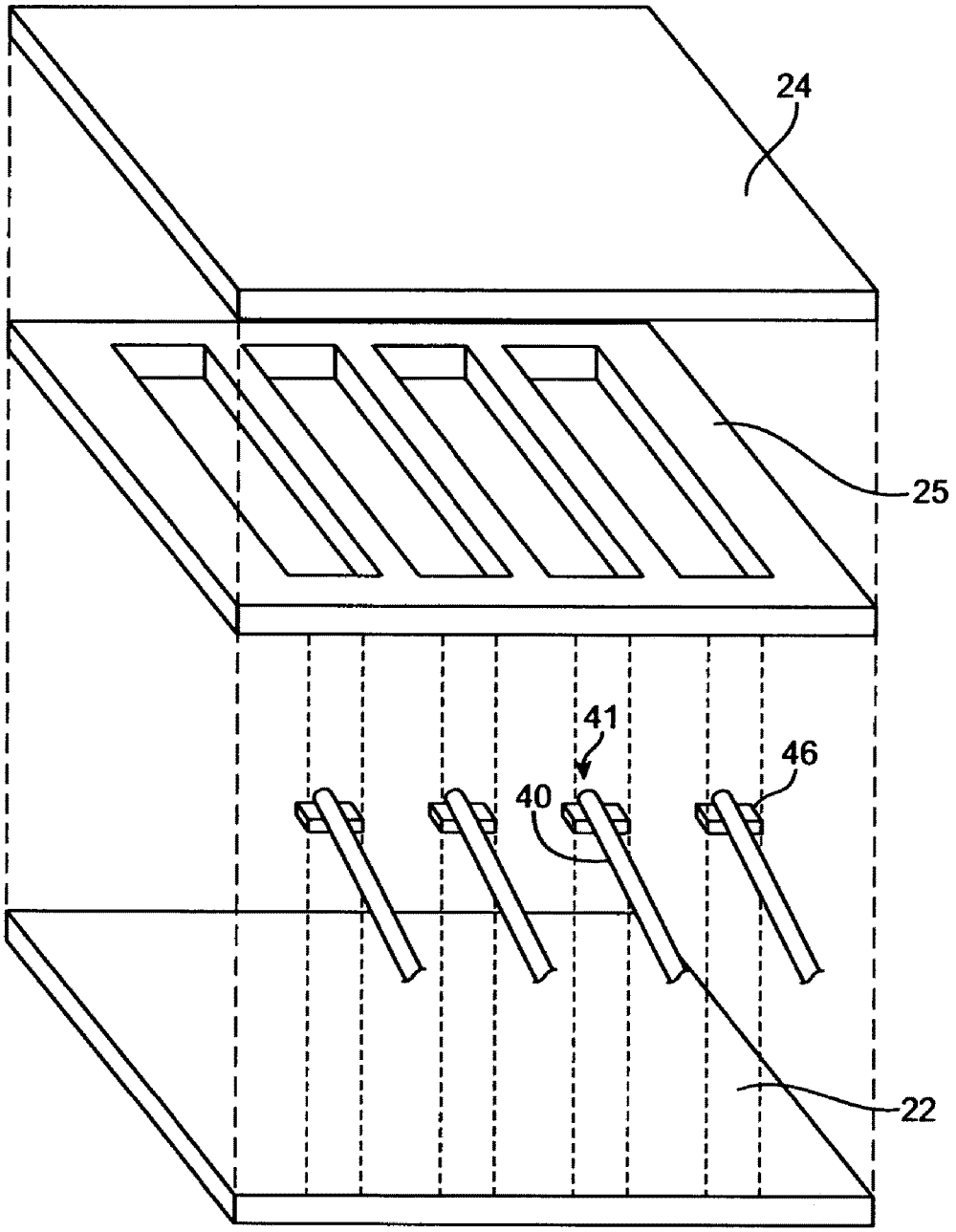

FIG. 9 is an illustration of a first system for manufacturing the present invention using three separate layers of material.

Figure 10:
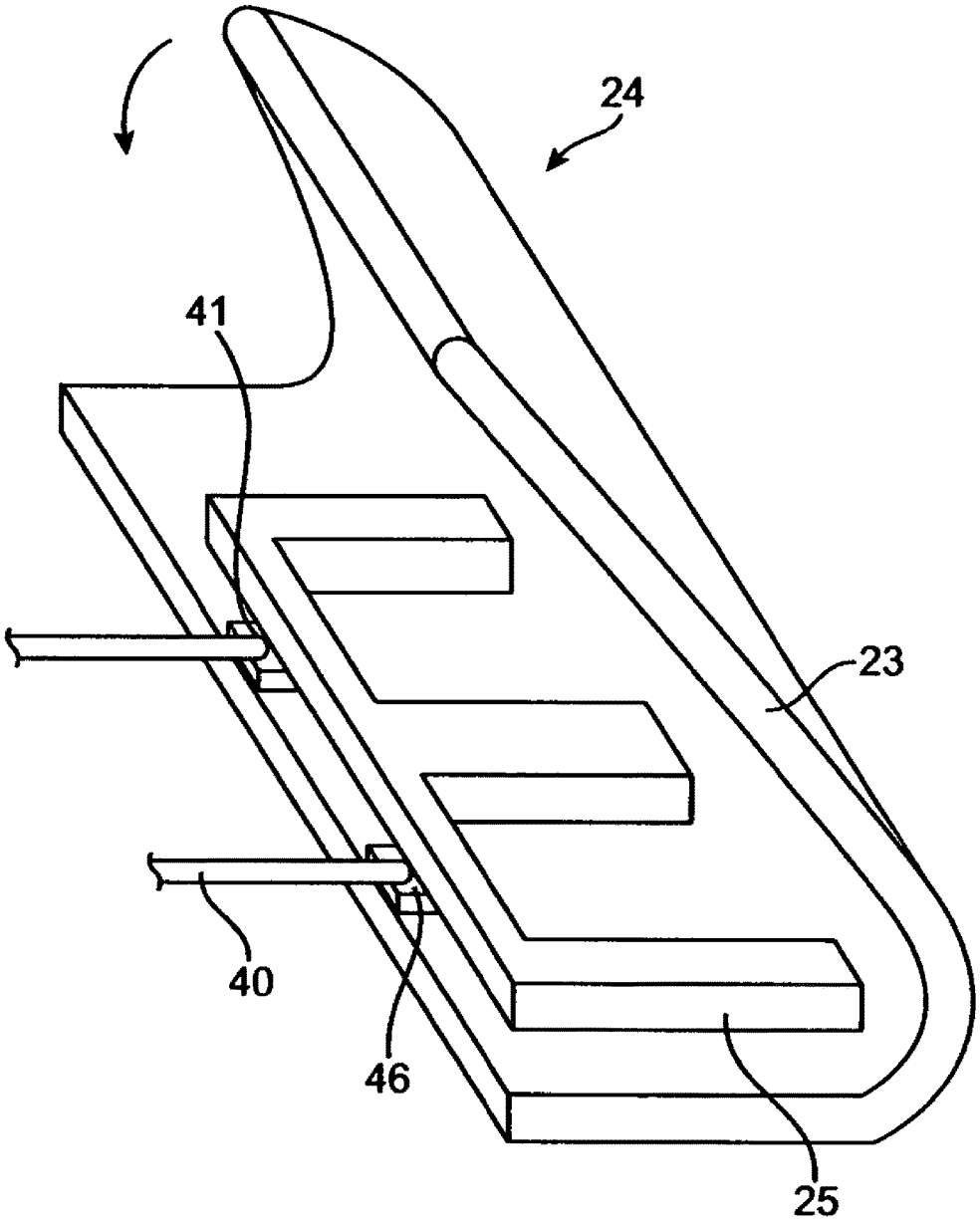

FIG. 10 is an illustration of a second system for manufacturing the present invention using one layer of material folded on top of itself with a second layer of material inserted therebetween.

Figure 11:
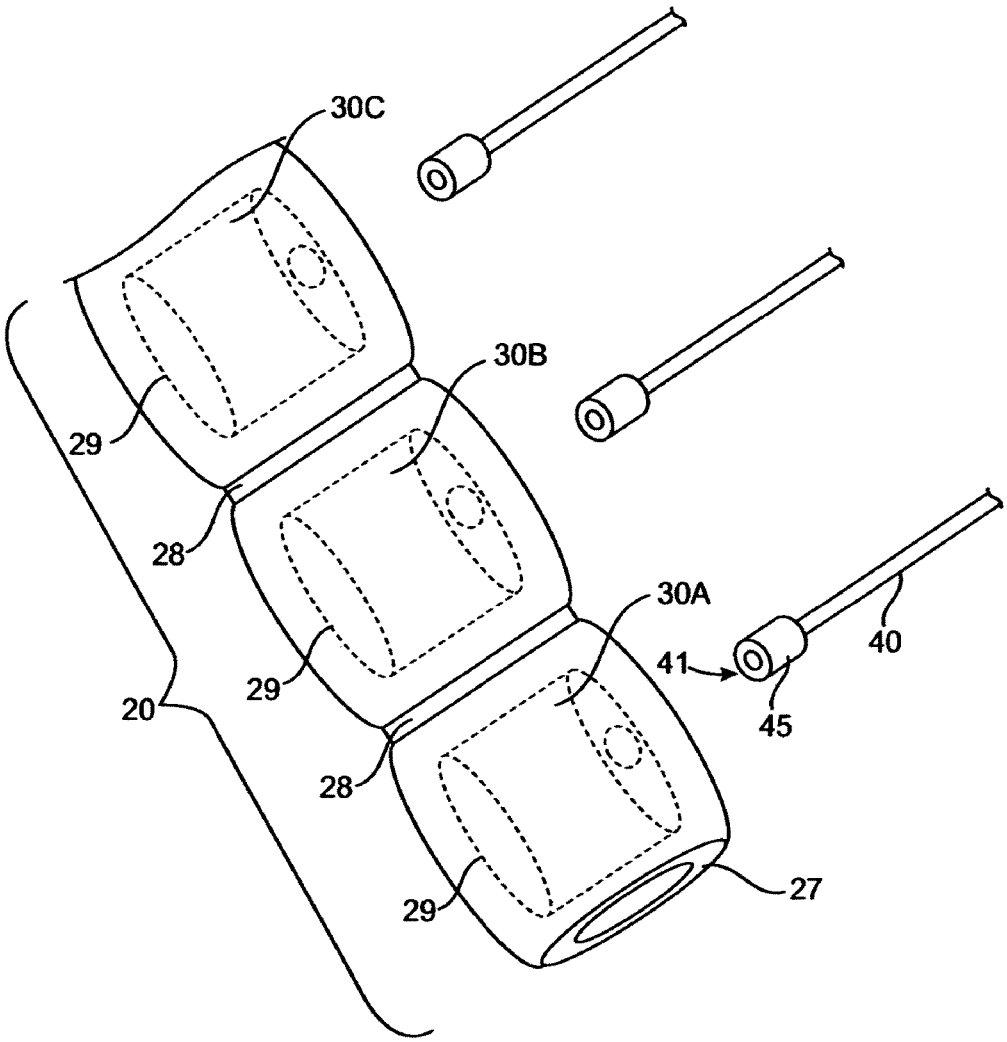

FIG. 11 is an illustration of a third system for manufacturing the present invention using one layer of material having regions that are pinched onto itself to be bound together, showing the insertion of filling tubes into the separate fillable-chambers.

Figure 12:
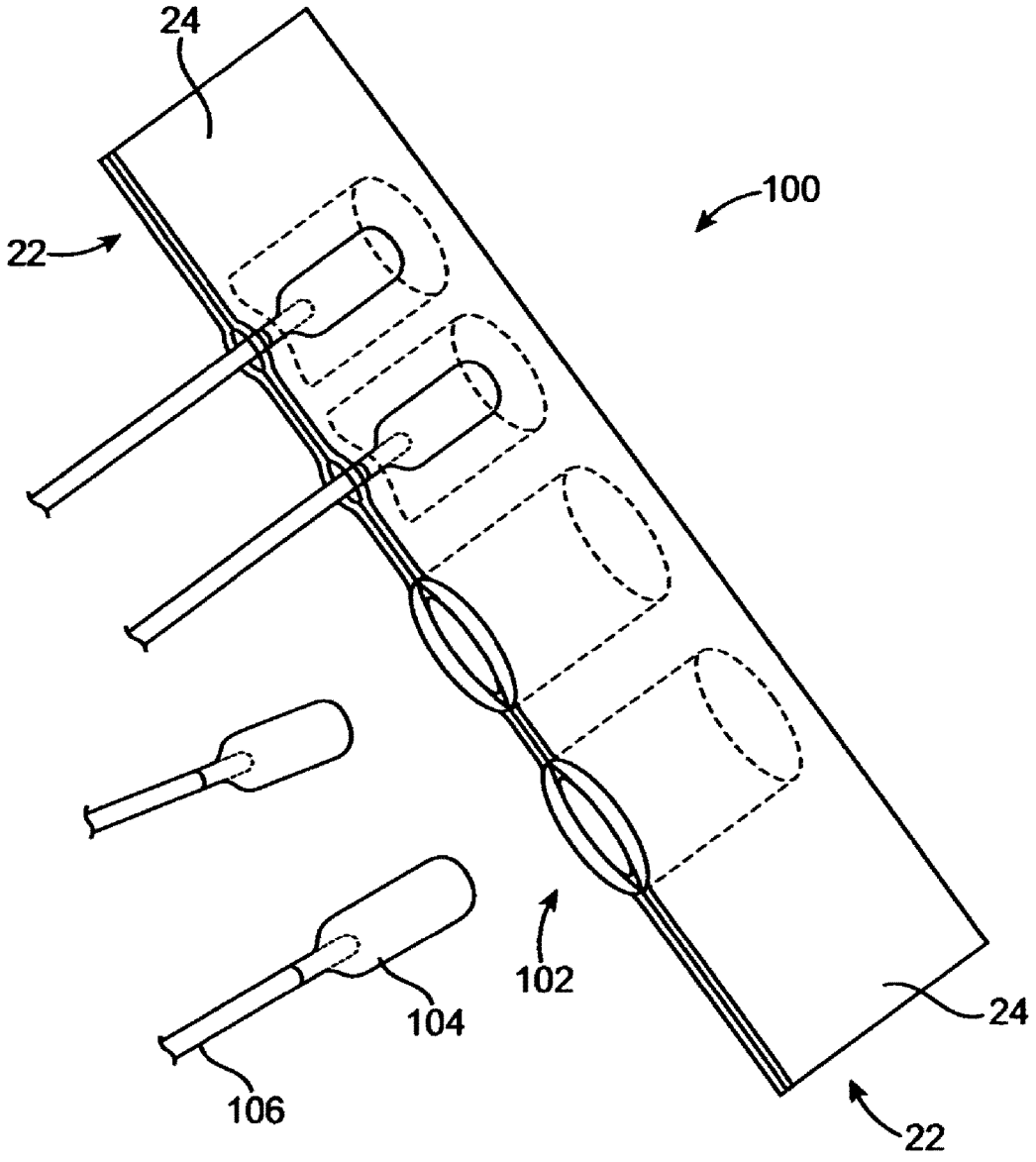

FIG. 12 is an illustration of an alternate embodiment of the invention having pockets in the device with fillable chambers inserted therein.

Figure 13:
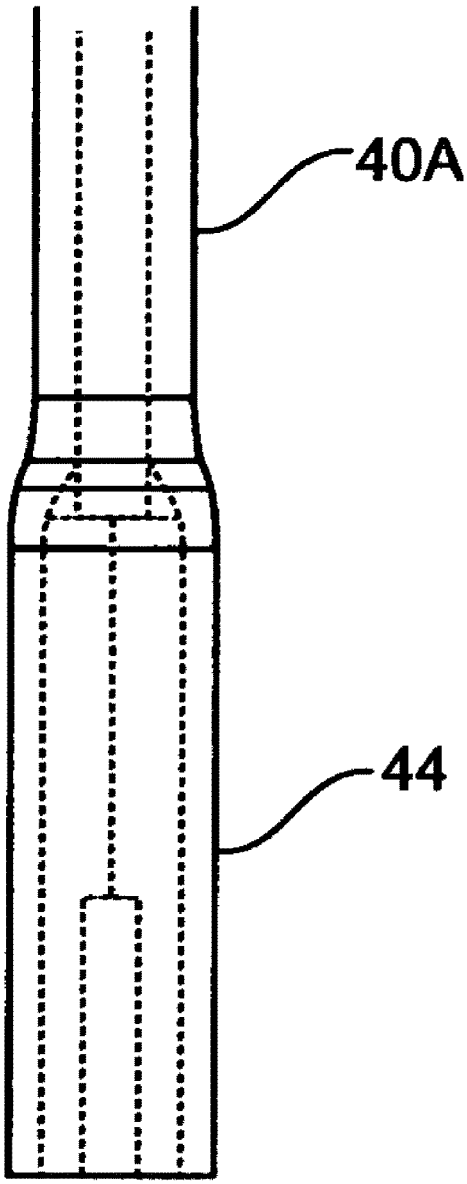

FIG. 13 is an illustration of the blunt needle port used to fill and deflate one or more fluid chambers.

DETAILED DESCRIPTION OF THE INVENTION

The present invention is directed to modifying heart valve function by applying localized support or pressure to various regions of the heart. In addition, the present invention may optionally be used to decrease, and/or prevent increases in, the dimensions of the base, and in particular the atrio-ventricular junction, beyond a pre-determined size.

In particular procedures, the present invention is directed to applying pressure to tissue adjacent to the mitral and/or tricuspid heart valves. This has the effect of beneficially modifying the shape of the heart valve(s) to treat heart valve dilation. As such, this invention is particularly suited for use in regurgitation of the mitral and tricuspid valves. However, the device may also optionally be used prophylactically in heart failure surgery to prevent further cardiac basal dilation or expansion even if the underlying mitral and tricuspid valves are competent. As such, the present device may be used in moderate or advanced heart failure to prevent progression of basal dilation or reduce the size of the dilated base.

As used herein, "atrio-ventricular" or A-V groove refers to the junction between the atrial and ventricular chambers of the heart, also known as the atrio-ventricular junction marked externally by the atrio-ventricular groove. This is easily identified in the change of appearance of the cardiac muscle and also the presence of arteries and veins. The "cardiac base", as used herein, is the area of the heart between and including the AV groove and extends to, but not including, the bottom or apex of the heart.

The heart is enclosed within a double walled sac known as the pericardium. The inner layer of the pericardial sac is the visceral pericardium or epicardium. The outer layer of the pericardial sac is the parietal pericardium. The term "endocardial surface" refers to the inner walls of the heart. The term "epicardial surface" refers to the outer walls of the heart.

The mitral and tricuspid valves sit at the base of the heart and prevent blood from leaking back into the atria or collecting chambers. See FIG. 1. Mitral regurgitation is a condition whereby blood leaks back through the mitral valve into the left atrium. Over time, this creates a damming of blood in the lungs causing symptoms of shortness of breath. The left heart particularly the left ventricle has to pump a greater volume of blood as a result causing greater strain on this chamber.

Figure 2:
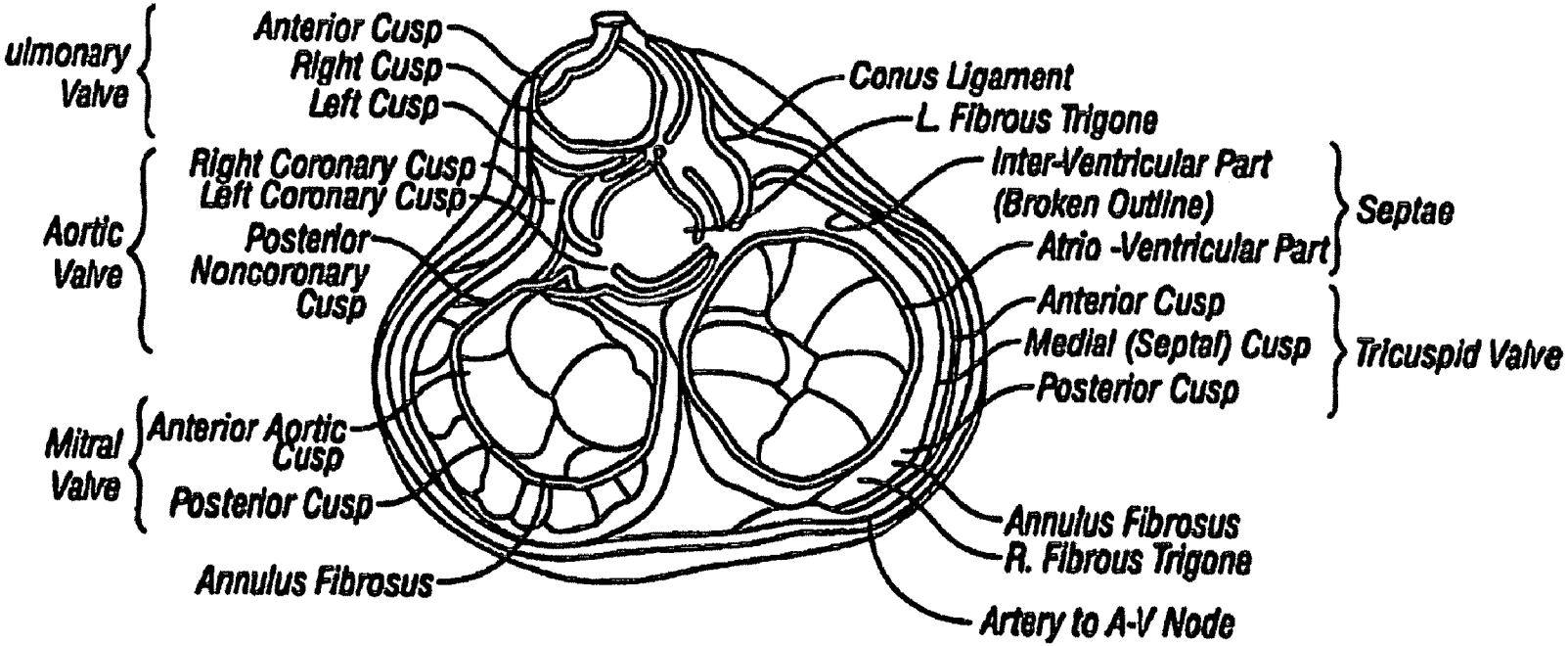
FIG. 2 depicts a cross-section of the base of the heart between the dashed lines depicted in FIG. 1.

Dilatation of the mitral annulus occurs maximally in the posterior portion of the annulus, which is not supported by the cardiac fibro-skeleton. FIG. 2 is an anatomic diagram of the base of the heart, showing the valves and the structures in contact with them. FIGS. 7A to 7D are various corresponding schematic representations of the valves at the cardiac base during placement and operation of the present device.

Mitral valve repair or replacement at present is always performed from inside the heart with the aid of cardiopulmonary bypass. Rings are implanted along the inner surfaces of the entire or expansile portions of the mitral and tricuspid annuli. Alternatively, when mitral valve malfunction is severe, replacement of the valve with a prosthetic valve may be indicated.

Overview

The basal ventricular stabilization, and heart valve shape re-shaping of the present invention works by using a band of prosthetic material such as silicone rubber being anchored or sutured to the base of the heart at the level of the atrio-ventricular groove. This band has at least one integral fillable chambers formed or inserted therein. In use, the present device serves to stabilize the mitral and tricuspid annuli from the outside (see FIGS. 7B and 7D). As will also be shown herein, this also serves to provide a device that applies pressure to tissue regions adjacent to the heart valves (e.g.: mitral and/or tricuspid valves) to re-shape the heart valve itself as a method of treating valve dilation problems.

The present invention and technique reduces the complexity of the procedure and minimizes the invasive nature and complications from work on the valve. This system and technique is of particular benefit in patients that have morphologically normal valves with annular dilatation. The device can be applied and anchored to the cardiac base, with the heart beating, without the aid of cardiopulmonary bypass.

Many patients with moderate degrees of mitral regurgitation are not treated surgically, because the risks of surgery outweigh the potential benefits in this group of patients. However, patients with conditions such as chronic heart failure tend to get very symptomatic even with moderate degrees of mitral regurgitation. These groups of patients would benefit from the less invasive procedures, which are the subject of the present invention. Thus, the potential of this technique in treating mitral regurgitation as a minimally invasive procedure has great appeal as the population ages and more patients manifest with symptoms of heart failure. It also can be applied in patients undergoing open heart coronary artery surgery without the aid of a heart-lung machine.

Device Parameters

The device of the present invention can be constructed of any suitable implantable material. In preferred embodiments, the device is constructed from layers of silicone rubber. An advantage of using such a material is that the device is sufficiently flexible to move with the expansion and contraction of the heart without impairing its function. It should, however, be designed to prevent expansion of the cardiac base during diastolic filling of the heart to a predetermined size. Since the size expansion parameters of a beating heart are well known, this can be accomplished by testing the device in vitro by applying forces that mimic heart expansion.

Figure 3:
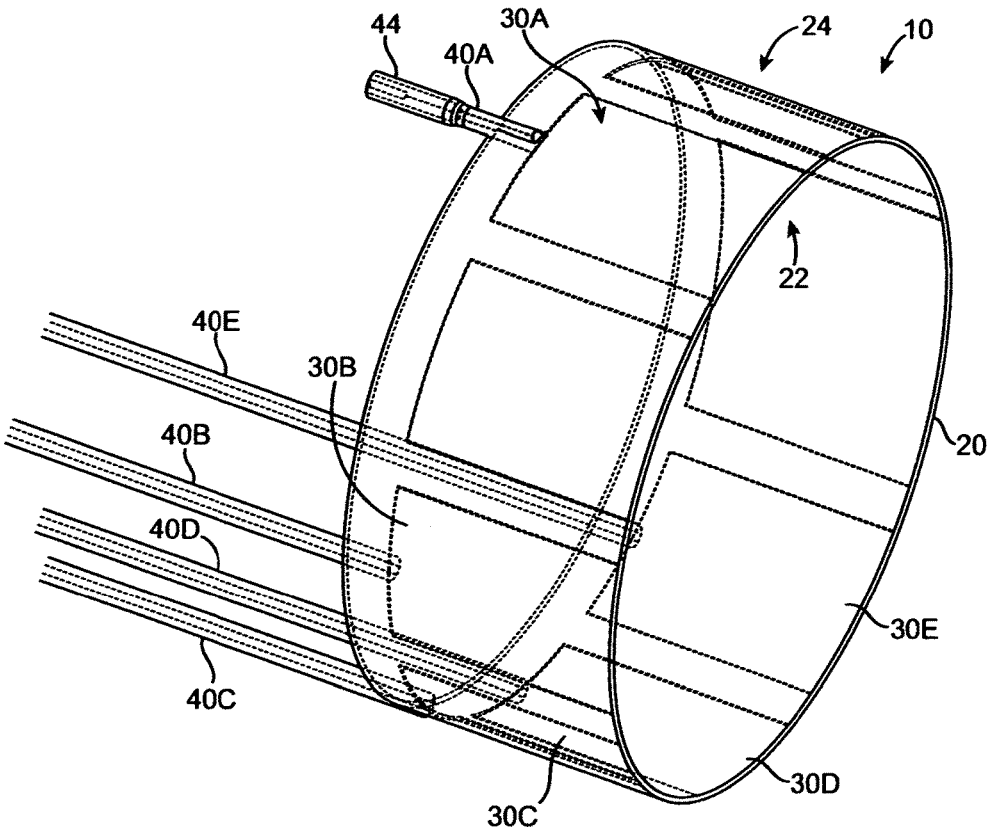
FIG. 3 is a perspective view of a representative embodiment of the device of the present invention.

As shown in FIG. 3, in one embodiment, the device 10 comprises a band 20 dimensioned to be received around a patient's heart. Band 20 comprises an inner layer 22 and an outer layer 24. In accordance with the present invention, areas of inner layer 22 and outer layer 24 are bound to one another, resulting in a very thin system design as can be seen. A unique advantage of such a thin band 20 is that it can easily be placed around the patient's heart during surgery.

Band 20 further comprises at least one fillable chamber 30 integrally formed therein. As depicted in FIG. 3, the band comprises five fillable chambers 30A-E. Specifically, fillable chambers 30 are located in areas where inner layer 22 and the outer layer 24 are not bound to one another. As will be fully explained below, fillable chambers 30 may be integrally formed into band 20 when inner layer 22 and outer layer 24 are selectively bound together to create an enclosure. Alternatively, however, fillable chambers 104 may be separately constructed and inserted into the areas where inner layer 22 and outer layer 24 are not bound to one another in the manufacturing of device 100 as seen in FIG. 12. For example, fillable chambers 104 may be inserted into individual "pockets" formed between inner layer 22 and outer layer 24. These pockets may be formed by attaching inner layer 22 and outer layer 24 along two sides and a first edge, keeping the second opposite edge (and the interior of the pocket) unbound until the individual chambers are inserted. The pocket openings would then be bonded closed or other means would be used to secure the individual fillable chambers.

In one exemplary embodiment, band 20 is formed from silicone rubber and is therefore transparent. However, the present invention is not so limited. For example, it is to be understood that band 20 may also be formed from other suitable biocompatible implantable materials, including, but not limited to a textile made from polyester, PTFE (polytetrafluoroethylene), or elastic yarns.

An advantage of forming band 20 (and its fillable chambers 30) from a transparent material is that it facilitates placement of the device around the patient's heart. In particular, the external vasculature of the heart is clearly viewable through band 20 as band 20 is placed around the patient's heart. Moreover, the transparent nature of the material permits easy positioning of fillable chambers 30 at preferred locations adjacent to heart valves (e.g., the mitral and/or tricuspid valve), and away from the vasculature.

In various embodiments, inner layer 22 and outer layer 24 may be bound to one another by adhesives, crosslinking (e.g., when layers 22 and 24 are pressed together and heated), or even by stitching. It is therefore to be understood that the present invention is not limited to any particular system of attachment or bonding of layers 22 and 24 together.

In various optional embodiments, an interior surface of inner layer 22 may be textured. This may advantageously assist in holding band 20 at a preferred position on the patient's beating heart. It is important, however, that the interior surface of inner layer 22 not be so textured such that it would adhere too strongly to the exterior of the heart, since this would make band 20 difficult to remove.

Figure 5:
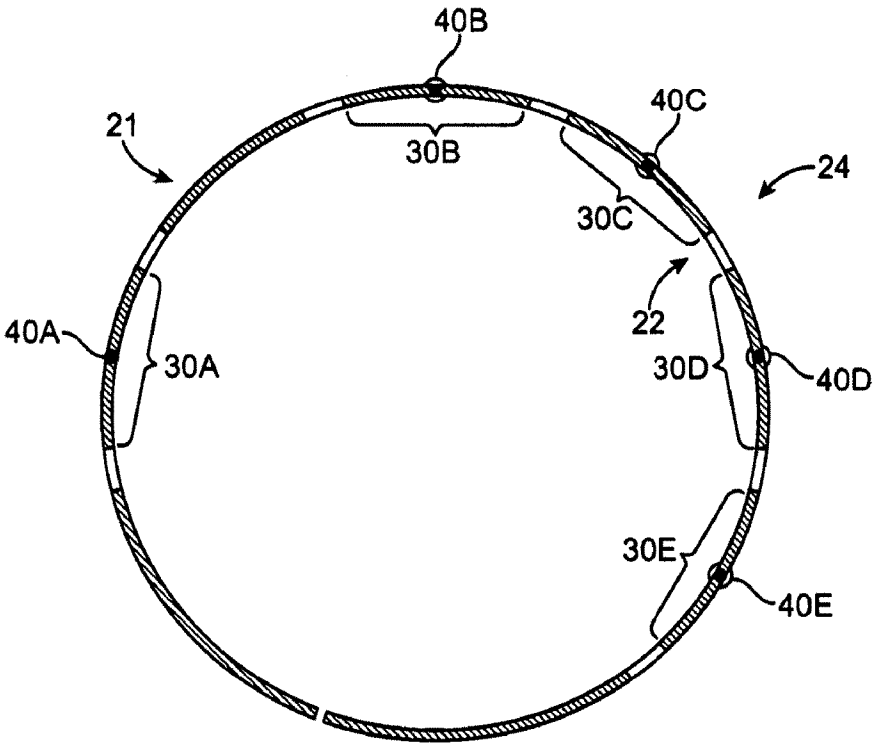
FIG. 5 is a proximal end view of the embodiment of the device of FIG. 3.
Figure 4:
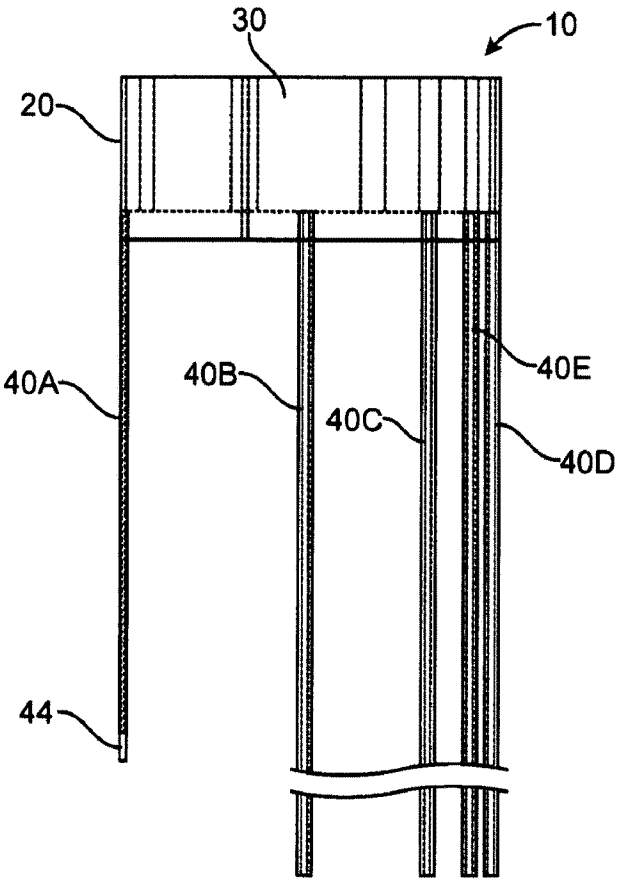
FIG. 4 is a side elevation view of the embodiment of the device of FIG. 3.

As seen in FIGS. 4 and 5, band 20 preferably has a plurality of fillable chambers 30. In FIG. 4, one such exemplary chamber 30 is depicted. As illustrated in FIG. 5, band 20 has five fillable chambers, being 30A, 30B, 30C, 30D and 30E. It is to be understood that this is only one exemplary embodiment, and that other embodiments of the invention have more or less than five fillable chambers 30. As such, the present invention encompasses any embodiment having at least one fillable chamber 30.

As also seen in FIG. 5, two of the plurality of fillable chambers 30 may be positioned spaced apart from one another, such that band 20 has a gap 21 between chambers 30A and 30B as depicted which forms a bridge between the chambers when applied to a patient's heart. Preferably, band 20 and fillable chambers 30A and 30B are dimensioned such that the gap 21 is dimensioned to be positioned over vasculature on the exterior of the heart when fillable chambers 30A and 30B are filled thus forming a bridge therebetween. Thus, fillable chambers 30A and 30B can be positioned on opposite sides of the pulmonary trunk of the heart. Bridges can also be formed between 30B and 30C, 30C and 30D, and 30D and 30E. An important advantage of these bridges is that they do not need to form a space between the heart and the band. Instead, they only need to reduce localized pressure so as to prevent vascular occlusion. A bridge or release of pressure can also be formed by filling only one chamber. Filling only one chamber creates pressure directly under that chamber, but it also relieves pressure directly on each side of that chamber.

As also seen in FIGS. 3 to 5, a number of filling tubes 40 are provided. Filling tubes 40 are preferably each in fluid communication with a separate fillable chamber 30, as illustrated in FIGS. 3 and 5.

Filing tubes 40 may be made of silicone, or other suitable material. Each filing tube 40 is in fluid communication with, and fills, its own dedicated fillable chamber 30. For example, as depicted in FIG. 5, filling tube 40A fills fillable chamber 30A, etc. It is to be understood that the present invention is not limited as to any particular substance being used for filing fillable chambers 30. As such, the individual fillable chambers 30 may be filled with substances including, but not limited to, a saline solution, a hardening polymer, a gel, or even a gas. Moreover, it is also to be understood that different fillable chambers 30 may be filled with different substances from one another.

In various embodiments, the separate filling tubes 40 may be fillable through a blunt needle port 44 (for receiving blunt needle), a sharp needle port, or through a subcutaneous port. As such, different filling tubes 40 may be fitted with different ports at their proximal ends. For example, as shown in FIG.

6A, filling tube 40A may be a short filling tube specifically equipped for filling through a blunt needle port. As such, filling tube 40A can be filled by a syringe via a syringe tip with a blunt needle as depicted in FIGS. 6A and 6B.

The present device is initially presented to the surgeon as a flattened, flexible device that is easy to handle during an operation.

Figure 6A:
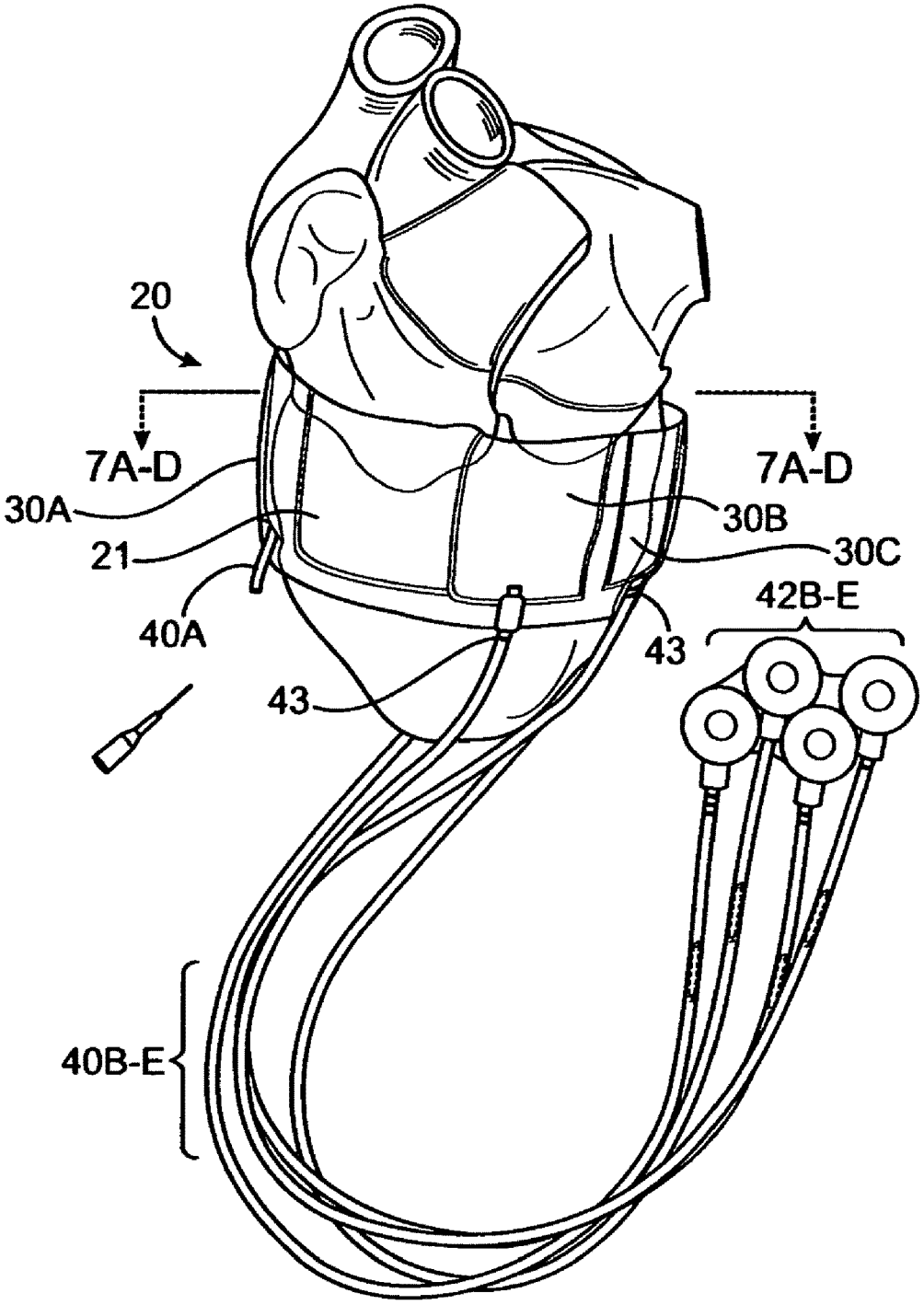
FIG. 6A is a perspective view of the device of FIG. 3, shown received around a patient's heart, prior to filling of the fillable chambers.
Figure 6B:
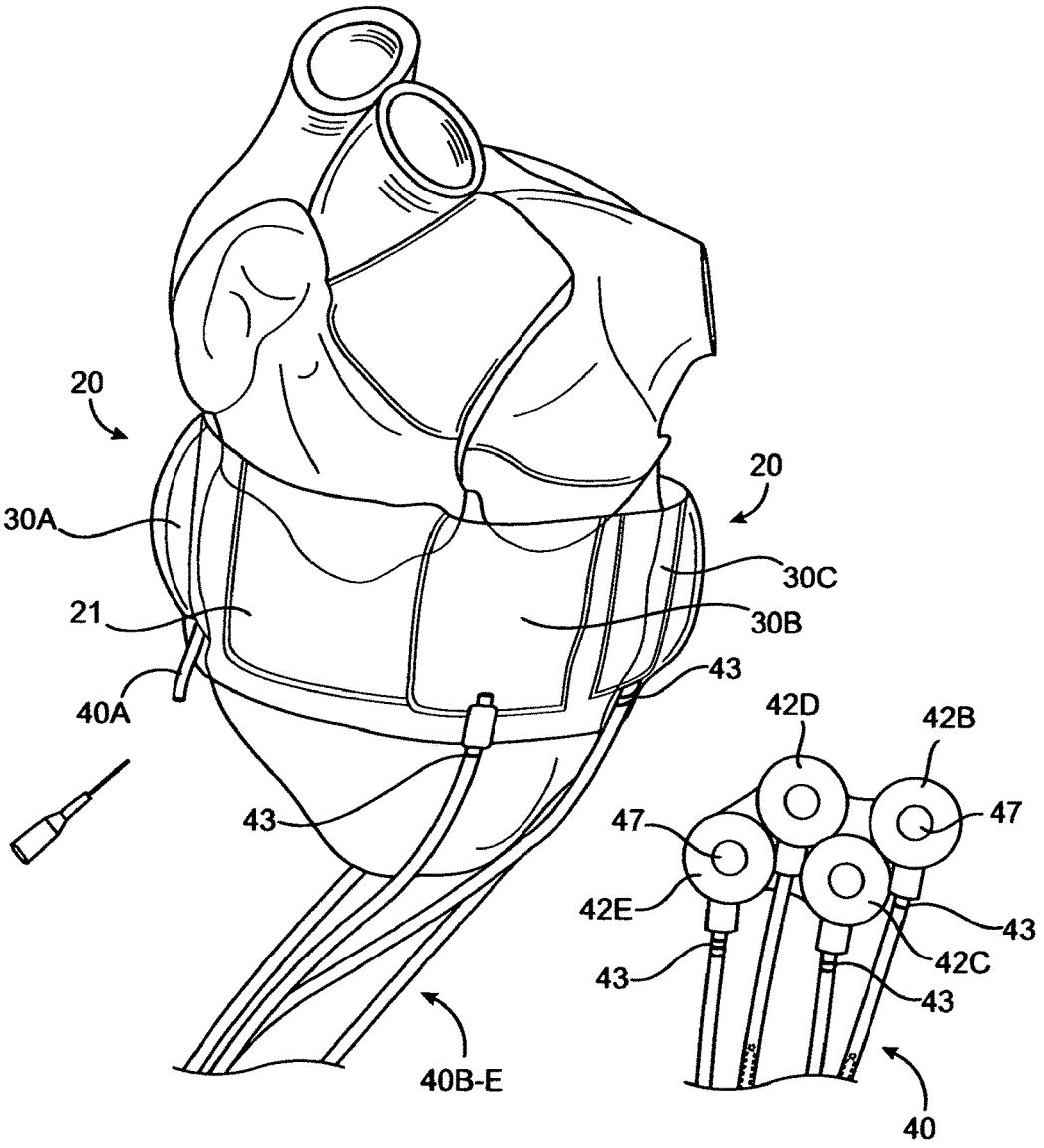
FIG. 6B is a perspective view of the device of FIG. 3, shown received around a patient's heart, after filling of the fillable chambers.

FIGS. 6A and 6B show perspective views of the present device 10, with the band 20 as positioned around the patient's heart, with the fillable chambers unfilled (FIG. 6A) and filled (FIG. 6B).

As seen in FIGS. 6A and 6B, in one embodiment of the present invention, device 10 comprises a band 20 having five fillable chambers 30A to 30E, and with each fillable chamber having its own dedicated filling tube 40A to 40E. As can also be seen, each of filling tubes 40B to 40E are fillable through a subcutaneous port 42B to 42E. The subcutaneous port(s) provide a unique feature to the invention with regards to heart valve repair in that they allow a surgeon to make post-operative adjustments to the implant without making any incisions. This is done by inserting a small gauge needle into the subcutaneous ports and injecting or withdrawing biocompatible fluid as needed. The subcutaneous port is made of silicone rubber or other biocompatible material that can be penetrated with a hypodermic needle and then reseal after removal of the needle.

Each subcutaneous port also may optionally include a biocompatible radiopaque metal drawn "can" 47 inside as depicted in FIG. 6B to facilitate locating the port by tactile feedback on the needle and syringe and by imaging on X-ray or fluoroscopy, which will also allow the needle to engage the port without enentrating it completely.

Optionally, subcutaneous ports 42B to 42E are disposed on a sheet (not depicted). This sheet may be made of silicone or polyester, or any other suitable material, or any combinations thereof. A sheet has the advantage of holding subcutaneous ports 42B to 42E together for convenient access. Preferably, the sheet (and subcutaneous ports 42B to 42E attached thereto) is surgically positioned on the lower side of the chest.

In preferred embodiments, each filing tube 40A to 40E may include a unique marker or indicia 43 (as shown in FIGS. 6A and 6B) such that the surgeon is able to clearly and easily identify which subcutaneous port 42 corresponds to which particular fillable chamber 30. For example, one radiopaque marker may be affixed to filling tube 40A, two radiopaque markers may be affixed to filling tube 40B, etc. Other versions of indicia in addition to radiopaque markers are contemplated within the scope of the present invention.

After band 20 has been positioned around the heart, saline may be introduced first with a blunt needle through a blunt needle port of filling tube 40A, and then through subcutaneous ports 42B to 42E to thus fill fillable chambers 30A to 30E. Since fillable chambers 30A to 30E can be selectively individually filled, it is possible for the surgeon to adjust the fitting of band 20 on the patient's heart with great accuracy. As such, each of fillable chambers 30A to 30E can be filled to a desired level and placed around the heart such that gap 21 and fillable chambers 30A to 30E are best positioned on the patient's heart to reshape the patient's heart valves as desired.

FIGS. 7A to 7D are cross sectional views of various of the devices at the location shown by the arrows in FIG. 6A. As such, they are a top-down cross sectional device immediately above the top edge of the device, giving the chambers a "pillow shape" configuration, with the closed edge of the "pillow" shown through the chambers 30. However, as discussed elsewhere in the specification, the band 20 actually consists of a separate inner layer 22 and outer layer 24, although not explicitly depicted in FIGS. 7A to 7D.

For example, as seen in FIGS. 7A and 7B, the shape of mitral valve MV may be modified by the filling of fillable chamber 30E. (FIG. 7A shows placement of the present band 20 prior to filling of fillable chamber 30E. FIG. 7B shows placement of the present band 20 after filling of fillable chamber 30E.). As can be seen, the poorly sealing mitral valve MV shown in FIG. 7A is re-shaped to seal properly in FIG. 7B. Chambers 30A and 30B as depicted in FIG. 7B are not filled to a degree necessary to reshape the pulmonary valve (PV), although they could be if such an effect was desired.

Alternatively, as seen in FIGS. 7C and 7D, the shape of mitral valve MV may instead be modified by the filling of fillable chamber 30D. (FIG. 7C shows placement of the present device 20 prior to filling of fillable chamber 30D. FIG. 7D shows placement of the present device 20 after filling of fillable chamber 30D.). As can be seen, the poorly sealing mitral valve MV shown in FIG. 7C is reshaped to seal properly in FIG. 7D.

As can also be seen in FIGS. 7A through 7D, band 20 forms a bridge corresponding to gap 21 between two of the fillable chambers, 30A and 30B. (Similar bridges can also be formed in band 20 between successive fillable chambers 30, or between a single fillable chamber 30 and the portion of the band adjacent thereto.)

As can be seen, the thin nature of band 20, coupled with the potentially large volumes of individually fillable chambers 30 produces a system in which pressure can be directed not only radially inward towards the center of heart, but also a "pinching" effect can be generated between adjacent fillable chambers 30.

As can be seen, by using different filling levels for each of the different fillable chambers 30, a system is provided in which pressures on the heart can be applied in an infinite number of different directions, and amplitudes. As such, pressures may be applied radially inwardly to the heart, as well as in non-radial directions (i.e., "pinching") portions of the heart therebetween.

FIG. 8 is a perspective view of a second representative embodiment of the device of the present invention having a plurality of ingrowth sleeves 50 received around band 20 for attachment to the exterior of the heart. In use, sleeves 50 operate like belt loops to hold up the band like a belt, thus holding band 20 in positions against the patient's beating heart.

Sleeves 50 are positioned on an exterior surface (i.e., outer side) of layer 24 as seen in FIG. 8. Sleeves 50 may optionally be made of polyester, or any other suitable material, including, but not limited to other woven, knitted, matted, or other textiles. Sleeves 50 in the preferred embodiment act as promoters of controlled tissue growth such that they become secure to selected areas of the heart, but they may also act to limit tissue growth and just provide mechanical means of attachment. Sleeves 50 may optionally be produced by molding them directly into a tension band. Sleeves 50 may optionally be fitted onto band 20 by sutures or staples.

FIGS. 9 to 11 show three different methods for producing the present device 10, including band 20 with chamber(s) 30 and optional filling tubes 40. It is to be understood that the device of the present invention is not limited to devices made by any particular system of manufacture. However, it is also to be understood that the present invention includes a variety of novel methods of manufacture of the device.

FIG. 9 is an illustration of a first system for manufacturing the present invention using three layers of material. Specifically, the view of FIG. 9 is an exploded view showing three layers of material as sandwiched together to form the present invention.

In this method of making the invention, a first layer of material (i.e.: layer 22) and a second layer of material (i.e. layer 24) are provided. Layers 22 and 24 may optionally be made of vulcanized silicone rubber, but may also be made of any other suitable material. In various embodiments, layers 22 and 24 may be made of the same materials, or be made of different materials. In addition, layers 22 and 24 may be made to the same thickness, or be made to different thicknesses.

A middle layer 25 is positioned between layers 22 and 24. Middle layer 25 may be made of separate sections of non-cured or non-vulanized silicon rubber. Middle layer 25 has sections removed that define and correspond to the locations of fillable chambers 30. Specifically, the presence of removed sections in middle layer sections 25 will allow layers 22 and 24 to contact one another (and be bound together) in those regions where middle layer sections 25 are disposed.

In accordance with the present method, layers 22, 25, and 24 may be bound together by applying pressure and heating such that they cure and fuse together. Alternatively, layers 22 and 24 can be bound directly together without 25 if they were non-vulcanized sheets of silicone rubber and then crosslinked together when these two layers are under pressure and heated at selective bond points.

As can be seen, the regions in which middle layer sections 25 are not positioned will form "pockets" between layers 22 and 24 (since middle layer 25 is not present which prevents layers 22 and 24 from becoming bonded to one another). These "pockets" defined by removed sections of middle layer 25 form the fillable chambers 30 in the band.

As can also be seen in FIG. 9, the distal ends 41 of filling tubes 40 may be inserted into the removed sections in middle layer 25. As a result, the distal ends 41 of filing tubes 40 are inserted within fillable chambers 30, while the bonding of layers 22 and 24 together secure in position the remaining end portion of filing tubes 40. A bonding tab 46 can be used to bind distal end 41 in position against layer 22 if needed to form a fluid tight chamber that communicates with tubing 40.

FIG. 10 is an illustration of a second system for manufacturing the present invention using one layer of material folded on top of itself with a second layer of material inserted therebetween.

In this second method of making the invention, a single layer of material 23 is used to form both inner layer 22 and outer layer 24. As can be seen, the single layer of material 23 is simply folded over upon itself. An advantage of this particular method of fabricating band 20 is that it avoids having to use two separate materials to form layers 22 and 24. This method also eliminates the creation of a seal all around the fillable chambers, so that fillable chambers 30 might be larger.

The method forming the device in FIG. 10 is similar to that set forth above with respect to forming the device of FIG. 9. Specifically, layer 23 is bonded, fused, cross-linked or adhered onto itself with removed sections in middle layer 25 forming the resulting fillable chambers 30. Similarly as well, the distal ends 41 of filling tubes 40 may be inserted in the removed sections of middle layer 25. As a result, the distal ends 41 of filing tubes 40 are inserted within fillable chambers 30, while the bonding of layer 23 onto itself secures in position the remaining end portion of filing tubes 40.

FIG. 11 is an illustration of a third system for manufacturing the present invention using a tube 27 of extruded non-cured or non-vulcanized silicon rubber. As tube 27 is extruded, regions 28 are pinched onto itself and are thus bound together. The regions of tube 27 that are not pinched together form the fillable chambers 30A, 30B and 30C. Tube 27 is extruded, and then separated along lines 29 into separate devices fillable chambers 30A, 30B and 30C, etc. Note: line 29 may simply be a line passing through a region of tube 27 that has been bound onto itself. As such, the ends of the separate devices 10A, 10B, etc. can be sealed. Thereafter, the distal ends 41 of fillable tubes 40 can be poked through side holes in band 20 and inserted into the separate fillable chambers 30. Thereafter, fillable tubes 40 can be adhesively bound into position, for example with a non-vulcanized silicone rubber tab 45 being rolled around, pressed in place, and heated to bond tubing 40 in position such that the tubing remains in fluid communication with fillable chambers 30.

FIG. 12 shows an alternate embodiment of the invention in which device 100 comprises a plurality of pockets 102 into which fillable chambers 104 are received. Each fillable chamber 104 has its own dedicated filling tube 106. Device 100 operates in a manner similar to device 10 as described above, with the only difference being that each fillable chamber is not integrally formed into band 20 as depicted in the previous embodiments, but the equivalent function of chamber 30 is now accomplished by the combination of a pocket 102 into which a separate fillable chamber 104 is inserted. These pockets into which fillable chambers 104 are received may simply be formed by bonding or attaching layers 22 and 24 along the sides and bottom edges of each pocket. Each fillable chamber is then bonded into place or layers 22 and 24 are bonded together to entrap each chamber in place.

Lastly, FIG. 13 shows a close-up view of the blunt needle port 44 that can be applied to the end of any of the tubing 40. (For example, as illustrated as tubing 40A in FIG. B. The blunt needle port 44 may be formed by injecting room temperature vulcanized (RTV) silicone rubber approximately half-way into a short piece of silicone rubber tubing. The RTV cures and then the first insertion of a blunt needle tears a slit in the RTV section creating a sealable slit and port. The section of tubing absent of RTV acts as a pilot to help locate, hold, seal, and guide the insertion of a blunt hypodermic needle. This blunt needle port 44 is then bonded into tubing 40 using RTV silicone rubber.

Device Size

Although the size of the device depends on the purpose for which it is being implanted, it is contemplated that the device will be wide enough (measured from the top edge, i.e. the atrium edge, to the outside of the second or bottom edge, i.e. the apex edge) to provide efficient support to the atrioventricular grove. Accordingly, in one embodiment, the device is between 2 and 5 centimeters wide. In other embodiments, the device may be adapted to provide support over a larger area of the heart. This would provide specifically for reinforcement of areas of scar or muscular weakness as in dyskinetic infracted areas of the myocardium.

Figure 1:
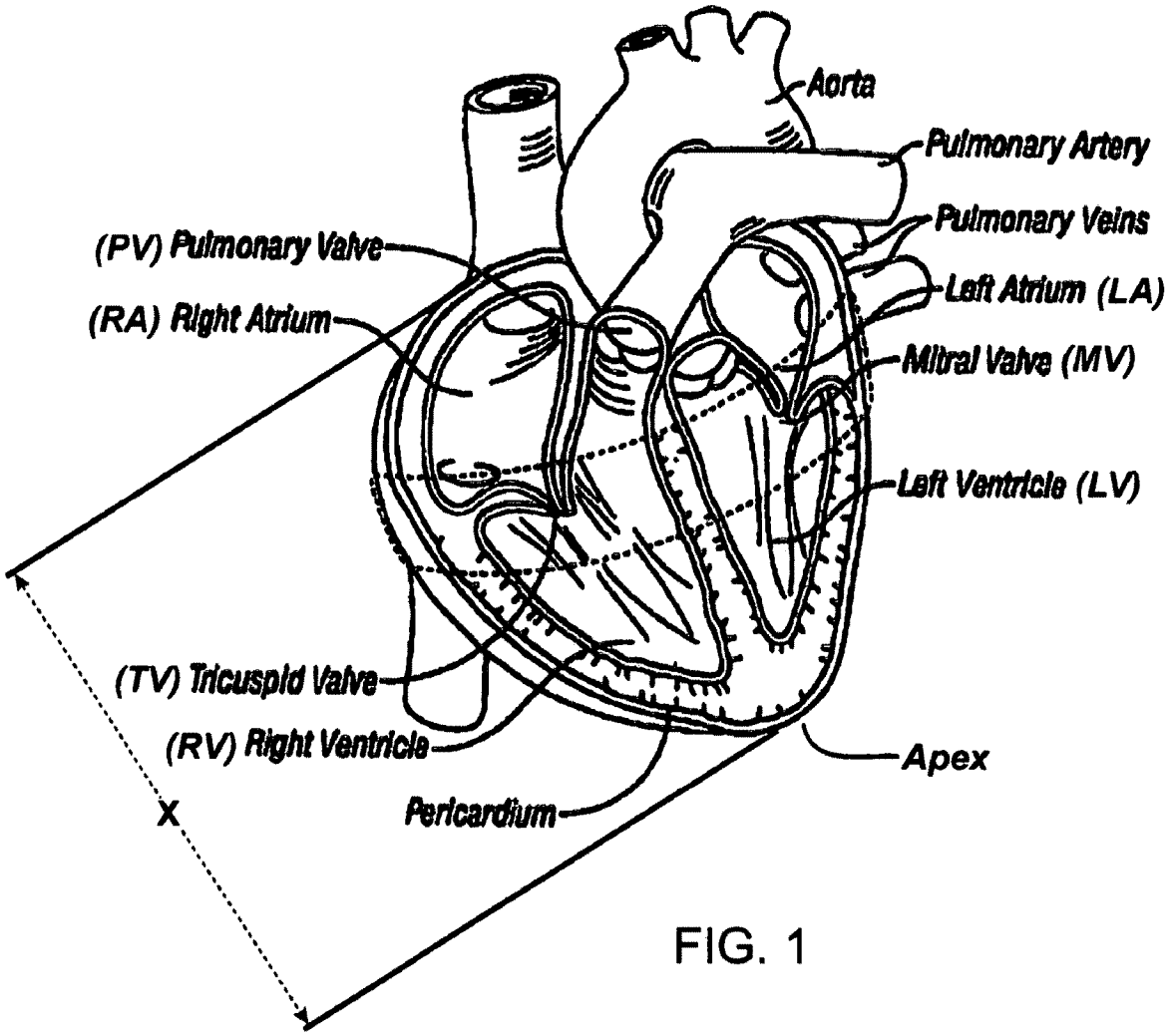
FIG. 1 depicts a cross-section of the heart, showing the approximate location of a representative embodiment of the device of the present invention by dashed lines, and the distance between the top and the bottom of the heart represented by "X".

As shown in FIG. 1, the distance between the base and the bottom of the apex of the heart can be expressed as distance "X". Because the focus of the device of the present invention is base stabilization, it is generally preferred that the width of the device be less than or equal to ½X, and be adapted for placement around the top half of the distance X, i.e. closer to the A-V Groove than the bottom of the apex.

Device Attachment

The device may be attached to the outside of the base of the heart by any known method. For example, attachment may be biological, chemical or mechanical. Biological attachment may be brought about by the interaction of the device with the surrounding tissues and cells, and can be promoted by providing appropriate enhancers of tissue growth. Alternatively, chemical attachment may be provided by supplying a mechanism for chemical attachment of the device, or portions thereof, to the external surface of the heart. In yet another embodiment, the rigidity and tightness of the device around the heart may provide for sufficient mechanical attachment due to the forces of the heart against the device without the need for other means of attachment.

In other alternate optional embodiments, the device instead further comprises attachment members, such as tabs. Specific anchor points or loops made of any biocompatible and implantable material may be attached to the edges or to the center portion or both to facilitate anchoring. Suitable materials include, inter alia, polyester, polypropylene or complex polymers. Alternative attachment members may comprise suture materials, protrusions that serve as sites for suturing or stapling, as well as other structural members that facilitate attachment to the surface of the heart.

Implantation

The BACE™ system may be implanted through a conventional midline-total sternotomy, sub maximal sternotomy or partial upper or lower sternotomy. Alternatively, the device may be implanted through a thoracotomy incision, or a Video Assisted Thoracoscopic (VAT) approach using small incisions. The BACE™ system can also be implanted by a subcostal incision as in the Sub-Costal Hand-Assisted Cardiac Surgery (SHACS). Additionally, the BACE™ system may be implanted with sutures onto epicardium or clips, staples, or adhesive material that can secure the device on the heart accurately. The device may also be implanted using robotic placement of the device along the posterior aspects of the base of the heart.

The method of implantation and the adequacy of the external annuloplasty can be dynamically assessed by intra-operative trans-esophageal echocardiography, epicardial echocardiography or trans-thoracic echocardiography. The size of the device is assessed based on external circumference measurements of the cardiac base in the fully loaded beating heart state.

EXPERIMENTAL RESULTS

The device was tested with good results with 4 fluid chambers around the mitral valve side of the heart. The fluid chambers were filled one at a time with contrast media (fluid visible under fluoroscopy), and were thus visible under fluoroscopy. Saline was first extracted from the chambers that was present during implantation from priming them. Next, about 4 cc of contrast media was injected into each chamber and a fluoroscopy picture was taken. The diameter across the mitral valve was measured before and after filling the chambers. The measurement before was 3.73 cm and then it reduced to 3.02 cm. This test shows that the mitral valve annulus can be reduced in diameter using the present invention.

What is claimed is:

1. An external heart device, comprising:

(a) a band dimensioned to be received around a patient's heart, the band comprising an inner layer and an outer layer, wherein some but not all areas of the inner layer and outer layer are bound to one another; [and]

(b) at least [two] *three* fillable chambers in the band, the at least [two] *three* fillable chambers being spaced apart from one another and located in areas where the inner layer and the outer layer are not bound to one another, [the] at least two *of the at least three* fillable chambers being separated by a gap, wherein the gap and each of the at least [two] *three* fillable chambers have a circumferential length, and wherein the circumferential length of the gap is greater than the circumferential length of each of the at least [two] *three* fillable chambers; *and*

*(c) a filling tube associated with each of said fillable chambers, wherein each of said fillable chambers is configured and arranged to be selectively individually filled, via an associated one of said filling tubes, whereby three different ones of said fillable chambers can be selectively filled to three different levels, respectively,* wherein the at least [two] *three* fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least [two] *three* fillable chambers are filled.

2. The external heart device of claim 1, wherein the at least [two] *three* fillable chambers are formed into the areas where the inner layer and the outer layer are not bound to one another.

3. The external heart device of claim 1, wherein the at least [two] *three* fillable chambers are inserted into the areas where the inner layer and the outer layer are not bound to one another.

4. The external heart device of claim 1, wherein the band is transparent.

5. The external heart device of claim 1, wherein the band is made of silicone rubber.

6. The external heart device of claim 1, wherein the inner layer and outer layer are bound to one another by adhesives.

7. The external heart device of claim 1, wherein the inner layer and outer layer are bound to one another by crosslinking.

8. The external heart device of claim 1, wherein the inner layer and outer layer are bound to one another by stitching.

9. The external heart device of claim 1, wherein an interior surface of the inner layer is textured.

10. The external heart device of claim 1, wherein the at least [two] *three* fillable chambers are a plurality of fillable chambers.

11. The external heart device of claim 10, wherein two of the plurality of fillable chambers are positioned spaced apart from one another, and wherein the band forms a bridge therebetween.

12. The external heart device of claim 11, wherein the bridge in the band is dimensioned to be positioned over vasculature on the exterior of the heart when at least one of the plurality of fillable chambers is filled.

13. The external heart device of claim 10, wherein the plurality of fillable chambers is five fillable chambers.

14. The external heart device of claim 1, further comprising a filling tube in fluid communication with the at least [two] *three* fillable chambers.

15. The external heart device of claim 14, wherein the filling tube is fillable through a blunt needle port.

16. The external heart device of claim 14, wherein the filling tube is fillable through a sharp needle port.

17. The external heart device of claim 14, wherein the filling tube is fillable through a subcutaneous port.

18. The external heart device of claim 14, wherein the filling tube is made of silicone.

19. The external heart device of claim 14, wherein the filling tube comprises identifying indicia.

20. [The external heart device of claim 17,] *An external heart device, comprising:*

(*a*) *a band dimensioned to be received around a patient's heart, the band comprising an inner layer and an outer layer, wherein some but not all areas of the inner layer and outer layer are bound to one another;*

(*b*) *at least two fillable chambers in the band, the at least two fillable chambers being spaced apart from one another and located in areas where the inner layer and the outer layer are not bound to one another, the at least two fillable chambers being separated by a gap, wherein the gap and each of the at least two fillable chambers have a circumferential length, and wherein the circumferential length of the gap is greater than the circumferential length of each of the at least two fillable chambers; and*

(*c*) *a filling tube associated with each of said fillable chambers, wherein each of said fillable chambers is configured and arranged to be selectively individually filled, via an associated one of said filling tubes, whereby different ones of said fillable chambers can be filled to different levels,* wherein the at least two fillable chambers comprises a plurality of fillable chambers and wherein [a] *one of the* filling [tube] *tubes* is in fluid communication with each fillable chamber, and wherein each filling tube is fillable through a subcutaneous port, and wherein the plurality of subcutaneous ports are disposed on a sheet, *and*

*wherein the at least two fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least two fillable chambers are filled.*

21. The external heart device of claim 20, wherein the sheet is made of silicone or polyester.

22. The external heart device of claim 1, wherein the at least [two] *three* fillable chambers are filled by saline.

23. The external heart device of claim 1, wherein the at least [two] *three* fillable chambers are filled by a hardening polymer.

24. The external heart device of claim 1, wherein the at least [two] *three* fillable chambers are filled by a gas.

25. The external heart device of claim 1, wherein the at least [two] *three* fillable chambers are filled by a gel.

26. The external heart device of claim 1, further comprising at least one sleeve positioned around an exterior surface of the outer layer.

27. The external heart device of claim 26, wherein the at least one sleeve is made of polyester.

28. A method of modifying heart valve function, comprising:

placing a band around a patient's heart, the band comprising an inner layer and an outer layer, wherein areas of the inner layer and outer layer are bound to one another, and wherein at least two fillable chambers in the band are spaced apart from each other and are located in areas where the inner layer and the outer layer are not bound to one another, the at least two fillable chambers being separated by a gap, wherein the gap and each of the at least two fillable chambers have a circumferential length, the circumferential length of the gap being greater than the circumferential length of each of the at least two fillable chambers, the at least two fillable chambers positioned on the heart spaced apart from one another with the gap placed over heart vasculature to form a pressure-reducing bridge over the heart vasculature; and filling the at least two fillable chambers with a fluid to cause the at least two fillable chambers to contact and apply constant localized pressure to the heart in a predetermined location to modify *the shape of a single* heart valve [shape]*;*

*wherein said step of filling the at least two fillable chambers comprises filling a first one of said fillable chambers to a first level and filling a second one of said fillable chambers to a second level, wherein said first level is different from said second level.*

*29. An external heart device, comprising:*

(*a*) *a band dimensioned to be received around a patient's heart, the band comprising an inner layer and an outer layer, wherein some but not all areas of the inner layer and outer layer are bound to one another;*

(*b*) *at least two fillable chambers in the band, the at least two fillable chambers being spaced apart from one another and located in areas where the inner layer and the outer layer are not bound to one another, the at least two fillable chambers being separated by a gap, wherein the gap and each of the at least two fillable chambers have a circumferential length, and wherein the circumferential length of the gap is greater than the circumferential length of each of the at least two fillable chambers;*

(*c*) *a filling tube associated with each of said fillable chambers, wherein each of said fillable chambers is configured and arranged to be selectively individually filled, via an associated one of said filling tubes, whereby different ones of said fillable chambers can be filled to different levels; and*

(*d*) *an additional outer layer positioned outwardly of the filling tubes, wherein said additional outer layer is bound to the outer layer of the band, thereby resulting in the band including the inner layer located inwardly of the filling tubes and both the outer layer and the additional outer layer being located outwardly of the filling tubes,*

*wherein the at least two fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least two fillable chambers are filled.*

*30. The external heart device of claim 29, further comprising a tube bonding tab associated with each of the filling tubes, whereby the tube bonding tabs are bonded to an outer surface the inner layer of the band.*

*31. The external heart device of claim 29, wherein the additional outer layer includes sections removed therefrom, wherein each of the removed sections corresponds to one of the fillable chambers.*

*32. The external heart device of claim 29, wherein the additional outer layer includes sections removed therefrom, wherein each of the removed sections defines a pocket between the inner layer and the outer layer, and further wherein the pockets each form one of the fillable chambers.*

*33. The method of claim 28, wherein the band further comprises a filling tube associated with each of said fillable chambers; and an additional outer layer positioned outwardly of the filling tubes, wherein said additional outer layer is bound to the outer layer of the band, thereby resulting in the band including the inner layer located inwardly of the filling tubes and both the outer layer and the additional outer layer being located outwardly of the filling tubes, and further wherein said step of filling the at least two fillable chambers comprises passing the fluid through at least two of the filling tubes and into the at least two associated fillable chambers.*

*34. The external heart device of claim 1, wherein each of said filling tubes is fillable through a subcutaneous port.*

*35. The external heart device of claim 34, wherein a plurality of said subcutaneous ports are disposed on a sheet.*

*36. The method of claim 28, wherein the band includes at least three fillable chambers, and further wherein said step of filling the fillable chambers comprises filling a first one of said fillable chambers and a second one of said fillable chambers, without filling a third one of said fillable chambers.*

*37. An external heart device, comprising:*

*(a) a band dimensioned to be received around a patient's heart, the band comprising an inner layer and an outer layer, wherein some but not all areas of the inner layer and outer layer are bound to one another;*

*(b) at least two fillable chambers in the band, the at least two fillable chambers being spaced apart from one another and located in areas where the inner layer and the outer layer are not bound to one another, the at least two fillable chambers being separated by a gap, wherein the gap and each of the at least two fillable chambers have a circumferential length, and wherein the circumferential length of the gap is greater than the circumferential length of each of the at least two fillable chambers;*

*(c) a filling tube associated with each of said fillable chambers, wherein each of said fillable chambers is configured and arranged to be selectively individually filled, via an associated one of said filling tubes, whereby different ones of said fillable chambers can be filled to different levels; and*

*(d) a port in fluid communication with each of said filling tubes that is configured and arranged to enable filling and deflating an associated one of said fillable chambers,*

*wherein at least one of said ports is of a different type than the remainder of said ports, and*

*wherein the at least two fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least two fillable chambers are filled.*

*38. The external heart device of claim 37, wherein the type of each of said ports is selected from the group consisting of a blunt needle port, a sharp needle port, a subcutaneous port, and a Luer port.*

*39. An external heart device, comprising:*

*(a) a band dimensioned to be received around a patient's heart, the band comprising an inner layer and an outer layer, wherein some but not all areas of the inner layer and outer layer are bound to one another;*

*(b) at least two fillable chambers in the band, the at least two fillable chambers being spaced apart from one another and located in areas where the inner layer and the outer layer are not bound to one another, the at least two fillable chambers being separated by a gap, wherein the gap and each of the at least two fillable chambers have a circumferential length, and wherein the circumferential length of the gap is greater than the circumferential length of each of the at least two fillable chambers;*

*(c) a filling tube associated with each of said fillable chambers, wherein each of said fillable chambers is configured and arranged to be selectively individually filled, via an associated one of said filling tubes, whereby different ones of said fillable chambers can be filled to different levels; and*

*(d) a port in fluid communication with each of said filling tubes that is configured and arranged to enable filling and deflating an associated one of said fillable chambers,*

*wherein all but one of said ports comprise subcutaneous ports, and*

*wherein the at least two fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least two fillable chambers are filled.*

*40. The external heart device of claim 39, wherein said port that is not a subcutaneous port comprises a blunt needle port.*

*41. A method of modifying heart valve function, comprising:*

*placing a band around a patient's heart, the band comprising an inner layer and an outer layer, wherein areas of the inner layer and outer layer are bound to one another, and wherein at least two fillable chambers in the band are spaced apart from each other and are located in areas where the inner layer and the outer layer are not bound to one another, the at least two fillable chambers being separated by a gap, wherein the gap and each of the at least two fillable chambers have a circumferential length, the circumferential length of the gap being greater than the circumferential length of each of the at least two fillable chambers, the at least two fillable chambers positioned on the heart spaced apart from one another with the gap placed over heart vasculature to form a pressure-reducing bridge over the heart vasculature; and*

*filling the at least two fillable chambers with a fluid to cause the at least two fillable chambers to contact and apply constant localized pressure to the heart in a predetermined location to modify heart valve shape,*

*wherein said step of filling the at least two fillable chambers comprises filling a first one of said fillable chambers to a first level and filling a second one of said fillable chambers to a second level, wherein said first level is different from said second level,*

*wherein said step of filling the at least two fillable chambers comprises filling the first one of said fillable*

*chambers to the first level via a first type of port and filling the second one of said fillable chambers to the second level via a second type of port, and wherein said first type of port is different from said second type of port.*

*42. The method of claim 41, wherein said second type of port is configured and arranged to allow for post-operative changes to the fluid level of the associated fillable chamber, while said first type of port is not configured and arranged to allow for post-operative changes to the fluid level of the associated fillable chamber.*

*43. The method of claim 42, wherein said first type of port comprises a blunt needle port.*

*44. The method of claim 42, wherein said second type of port comprises a subcutaneous port.*

*45. An external heart device, comprising:*

*(a) a band dimensioned to be received around a patient's heart, the band comprising an inner layer and an outer layer, wherein some but not all areas of the inner layer and outer layer are bound to one another;*

*(b) at least two fillable chambers in the band, the at least two fillable chambers being spaced apart from one another and located in areas where the inner layer and the outer layer are not bound to one another, the at least two fillable chambers being separated by a gap, wherein the gap and each of the at least two fillable chambers have a circumferential length, and wherein the circumferential length of the gap is greater than the circumferential length of each of the at least two fillable chambers;*

*(c) a filling tube associated with each of said fillable chambers, wherein each of said fillable chambers is configured and arranged to be selectively individually filled, via an associated one of said fillable tubes, whereby different ones of said fillable chambers can be filled to different fluid levels;*

*(d) an additional outer layer positioned outwardly of the filling tubes, wherein said additional outer layer is bound to the outer layer of the band, thereby resulting in the band including the inner layer located inwardly of the filling tubes and both the outer layer and the additional outer layer being located outwardly of the filling tubes; and*

*(e) a port in fluid communication with each of said filling tubes that is configured and arranged to enable filling and deflating an associated one of said fillable chambers, wherein at least one of said ports is of a different type than the remainder of said ports;*

*wherein the at least two fillable chambers are positioned on the heart spaced apart from one another with the gap being placed over heart vasculature so as to form a pressure-reducing bridge over the heart vasculature contacting and applying constant localized pressure to the heart in a predetermined location to modify a heart valve shape when the at least two fillable chambers are filled.*

*46. The external heart device of claim 45, wherein all but one of said ports is of a first type and the single remaining port is of a second type, wherein said first type is different from said second type.*

*47. The external heart device of claim 45, wherein:*

*at least one of said ports is of a first type and the remainder of said ports are of a second type;*

*said first type is different from said second type; and*

*said second type of port is configured and arranged to allow for post-operative changes to the fluid level of the associated fillable chamber, while said first type of port is not configured and arranged to allow for post-operative changes to the fluid level of the associated fillable chamber.*

*48. The external heart device of claim 45, wherein:*

*said first type of port is a blunt needle port; and*

*said second type of port is selected from the group consisting of a sharp needle port, a subcutaneous port, and a Luer port.*

* * * * *